(12) United States Patent
Zisman

(10) Patent No.: US 11,927,594 B2
(45) Date of Patent: Mar. 12, 2024

(54) METHODS OF DETECTING AND TREATING PULMONARY HYPERTENSION

(71) Applicant: Rensselaer Center for Translational Research, Inc., Rensselaer, NY (US)

(72) Inventor: Lawrence S. Zisman, Slingerlands, NY (US)

(73) Assignee: RENSSELAER CENTER FOR TRANSLATIONAL RESEARCH, INC., Rensselaer, NY (US)

( * ) Notice: Subject to any disclaimer, the term of this patent is extended or adjusted under 35 U.S.C. 154(b) by 538 days.

(21) Appl. No.: 16/785,434

(22) Filed: Feb. 7, 2020

(65) Prior Publication Data

US 2021/0003583 A1    Jan. 7, 2021

Related U.S. Application Data

(63) Continuation of application No. 16/421,099, filed on May 23, 2019, now abandoned, which is a continuation of application No. 15/347,439, filed on Nov. 9, 2016, now abandoned.

(60) Provisional application No. 62/253,184, filed on Nov. 10, 2015.

(51) Int. Cl.
    *G01N 33/68*    (2006.01)
(52) U.S. Cl.
    CPC ..... *G01N 33/6827* (2013.01); *G01N 33/6848* (2013.01); *G01N 33/6893* (2013.01); *G01N 2440/14* (2013.01); *G01N 2458/15* (2013.01); *G01N 2800/12* (2013.01); *G01N 2800/321* (2013.01)

(58) Field of Classification Search
    CPC ........... G01N 33/6827; G01N 33/6848; G01N 33/6893; G01N 2440/14; G01N 2458/15; G01N 2800/12; G01N 2800/321
    See application file for complete search history.

(56) References Cited

U.S. PATENT DOCUMENTS

| 7,052,915 | B2 | 5/2006 | Aebersold et al. |
| 2004/0106150 | A1 | 6/2004 | Wang |
| 2005/0074824 | A1 | 4/2005 | Botfield et al. |
| 2008/0108795 | A1 | 5/2008 | Guo et al. |
| 2011/0269161 | A1* | 11/2011 | Gygi ................. G01N 33/6842 435/15 |

OTHER PUBLICATIONS

Marsboom (Circ Res 2012 110: 1484) (Year: 2012).*
Jang WI, et al. A specific inhibitor of 45 CDK1, R0-3306, reversibly arrests meiosis during in vitro maturation of porcine oocytes. Anim Reprod Sci. 2014;144(3-4):102-8.
Wang H, et al A2 phosphorylation after DNA damage by the coordinated action of ataxia telangiectasia-mutated and DNA-dependent protein kinase. Cancer Res.2001;61(23):8554-63.
Abdalla M, et al. The Akt inhibitor, triciribine, ameliorates chronic hypoxia-induced vascular pruning and TGFbeta-induced pulmonary fibrosis. Br J Pharmacol. 2015;172(16):4173-88.
Abdul-Salam VB, et al. Identification of plasma protein biomarkers associated with idiopathic pulmonary arterial hypertension. Proteomics. 2006;6(7):2286-94.
Abdul-Salam VB, et al. Proteomic analysis of lung tissues from patients with pulmonary arterial hypertension. Circulation. 2010;122(20):2058-67.
Abekhoukh S, et al. Dyrk1A, a serine/threonine kinase, is involved in ERK and Akt activation in the brain of hyperhomocysteinemic mice. Mol Neurobiol.2013;47(1 ):105-16.
Adayev T, et al. Harmine is an ATP-competitive inhibitor for dual-specificity tyrosine phosphorylation-regulated kinase 1 A (Dyrk1 A). Arch Biochem Biophys. 2011 ;507(2):212-8.
Alexeeva M, et al. The structure of a dualspecificity tyrosine phosphorylation-regulated kinase 1 A-PKC412 complex reveals disulfide-bridge formation with the anomalous catalytic loop HRD(HCD) cysteine. Acta Crystallogr D Bioi Crystallogr. 2015;71 (Pt 5):1207-15.
Antica, et al. Aberrant Ikaros, Aiolos, and Helios expression in Hodgkin and non-Hodgkin lymphoma. Blood, vol. 111, No. 6, 2008, pp. 3296-3297.
Antoniu SA. Targeting RhoA/ROCK pathway in pulmonary arterial hypertension. Expert Opin Ther Targets. 2012; 16(4 ):355-63.
"AquaPreserve TM DNA/RNA/Protein Order # Preservation and Extraction Kit," MoBiTec, Mar. 21, 2014 (Mar. 21, 2014), pp. 1-9. Retrieved from the internet :<http://www.mobitec.com/cms/products/bio/06_dna_prot_tools/extract_prod3.html?pdf=8001MT.pdf>on Feb. 8, 2017 (Feb. 8, 2017). entire document.
Azad A, et al. Inhibition of DNA-dependent protein kinase induces accelerated senescence in irradiated human cancer cells. Mol Cancer Res. 2011 ;9(12):1696-707.
Bagley MC, et al. Microwave-assisted synthesis of N-pyrazole ureas and the p38alpha inhibitor BIRB 796 for study into accelerated cell ageing. Org Biomol Chem. 2006;4(22):4158-64.
Barst RJ. PDGF signaling in pulmonary arterial hypertension. J Clin Invest. 2005;115(10):2691-4.

(Continued)

*Primary Examiner* — Changhwa J Cheu
(74) *Attorney, Agent, or Firm* — Seed IP Law Group LLP

(57) ABSTRACT

The present disclosure describes a method of quantifying amounts of phosphopeptides using isotopically-enriched peptides as internal standards. A kit comprising at least one isotopically-enriched phosphorylated peptide can be used to quantify changes in amounts of phosphopeptides using parallel reaction monitoring mass spectrometry techniques. The invention can be used to indicate the pathologic mechanism, severity of the disease, and treatment response of a subject. The invention can also be used to identify subjects who require more aggressive therapeutic interventions or alternative treatments.

9 Claims, 5 Drawing Sheets
Specification includes a Sequence Listing.

(56) References Cited

OTHER PUBLICATIONS

Becker W, et al. Activation, regulation, and inhibition of DYRK1A. FEBS J. 2011 ;278(2):246-56.

Behjati S, et al. Recurrent PTPRB and PLCG1 mutations in angiosarcoma. Nat Genet. 2014;46(4):376-9.

Billot, et al. Differential aiolos expression in human hematopoietic subpopulations. Leukemia Research, vol. 34, 2010, pp. 289-293.

Bock AS, et al. Effect of Gsk3 inhibitor CHIR99021 on 5 aneuploidy levels in rat embryonic stem cells. In Vitro Cell Dev Biol Anim. 2014;50(6):572-9.

Bolos M, et al. Oral administration of a GSK3 inhibitor increases brain insulin-like growth factor I levels. The Journal of biological chemistry. 2010;285(23):17693-700.

Buontempo F, et al. Cytotoxic activity of the casein kinase 2 inhibitor CX-4945 against T-cell acute lymphoblastic leukemia: targeting the unfolded protein response signaling. Leukemia. 2014;28(3):543-53.

Butler T, et al., Role of serine-threonine phosphoprotein phosphatases in smooth muscle contractility. Am J Physiol Cell Physiol. 2013;304(6):C485-504.

Chamberlain P, et al. Crystal structures of PRK1 in complex with the clinical compounds lestaurtinib and tofacitinib reveal ligand induced conformational changes. PloS one. 2014;9(8):e103638.

Chang W, et al., Phosphorylation of MAP4 affects microtubule properties and cell cycle progression. J Cell Sci. 2001; 114(Pt. 15):2879-87.

Chhina MK, et al., Evaluation of imatinib mesylate in the treatment of pulmonary arterial hypertension. Future Cardiol. 2010; 6(1):19-35.

Chilin A, et al. Coumarin as attractive casein kinase 2 (CK2) inhibitor scaffold: an integrate approach to elucidate the putative binding motif and explain structure-activity relationships. J Med Chem. 2008;51(4):752-9.

Choi WI, et al. Promyelocytic leukemia zinc finger-retinoic acid receptor alpha (PLZF-RARalpha), an oncogenic transcriptional repressor of cyclin-dependent kinase inhibitor 1A (p21WAF/CDKN1A) and tumor protein p53 (TP53) genes. J Biol Chem. 2014;289(27):18641-56.

Cole DE, et al., Plasma and cerebrospinal fluid pharmacokinetics of the Akt inhibitor, perifosine, in a non-human primate model. Cancer Chemother Pharmacol. 2015;75(5):923-8.

Compton DA, and Cleveland DW. NuMA, a nuclear protein involved in mitosis and nuclear reformation. Curr Opin Cell Biol. 1994;6(3):343-6.

Cortes, et al. Control of Lymphocyte development by the Lkaros Gene Family. Lymphocyte Development, Current Opinion in Immunology, vol. 11, No. 2, 1999, pp. 167-171.

Cozza G, et al. Exploiting the repertoire of CK2 inhibitors to target DYRK and PIM kinases. Biochim Biophys Acta.2013; 1834(7):1402-9.

Cozza G, et al. Quinalizarin as a potent, selective and cell-permeable inhibitor of protein kinase CK2. The Biochemical journal. 2009;421 (3):387-95.

Cozza G, et al.Synthesis and properties of a selective inhibitor of homeodomain-interacting protein kinase 2 (HIPK2). PloS one. 2014;9(2):e89176.

Crafter C, et al., Combining AZD8931, a novel EGFR/HER2/HER3 signalling inhibitor, with AZD5363 limits AKT inhibitor induced feedback and enhances antitumour efficacy in HER2-amplified breast cancer models. Int J Oncol. 2015; 47(2):446-54.

Cuny GD, et al. Structure-activity relationship study of acridine analogs as haspin and DYRK2 kinase inhibitors. Bioorg Med Chem Lett. 2010;20(12):3491-4.

Dai Y, et al. Induction of apoptosis in human leukemia cells by the CDK1 inhibitor CGP74514A. Cell Cycle. 2002;1(2):143-52.

De Kreuk BJ, et al., The human minor histocompatibility antigen 1 is a RhoGAP. PLoS One. 2013;8(9):e73962.

Dempsey EC, et al. Protein kinase C activation allows pulmonary artery smooth muscle cells to proliferate to hypoxia. Am J Physiol. 1991;260(2 Pt 1):L136-45.

Dennis M, et al Phase I study of the Aurora B kinase inhibitor barasertib (AZD1152) to assess the pharmacokinetics, metabolism and excretion in patients with acute myeloid leukemia. Cancer Chemother Pharmacol. 2012;70(3):461-9.

Dewerth A, et al., In vitro evaluation of the Aurora kinase inhibitor VX-680 for Hepatoblastoma. Pediatr Surg Int. 2012;28(6):579-89.

Duffy JP, et al. The Discovery of VX-745: A Novel and Selective p38alpha Kinase Inhibitor. ACS Med Chem Lett. 2011 ;2(1 0):758-63.

Duhamel, et al. The Aiolos transcription factor is up-regulated in chronic lymphocytic leukemia. Blood, vol. 111, No. 6, 2008, pp. 3225-3228.

Duong MT, et al., Hbo1 is a cyclin E/CDK2 substrate that enriches breast cancer stem-like cells. Cancer Res. 2013;73(17):5556-68.

Edwards WD, and Edwards JE. Clinical primary pulmonary hypertension: three pathologic types. Circulation. 1977;56(5):884-8.

Elliott SL, et al. Mitoxantrone in combination with an inhibitor of DNA-dependent protein kinase: a potential therapy for high risk B-cell chronic lymphocytic leukaemia. Br J Haematol. 5 2011;152(1):61-71.

Falchook GS, et al. Relative bioavailability of a prototype oral solution of the Aurora A kinase inhibitor alisertib (MLN8237) in patients with advanced solid tumors. Int J Clin Pharmacol Ther. 2015;53(7):563-72.

Farha S, et al. Imatinib in pulmonary arterial hypertension: c-Kit inhibition. Pulm Circ. 2014;4(3):452-5.

Fishman AP. Changing concepts of the pulmonary plexiform lesion. Physiol Res. 2000;49(5):485-92.

Frederick R, et al. Novel trisubstituted harmine derivatives with original in vitro anticancer activity. J Med Chem. 2012;55(14):6489-501.

Friedmann Y, et al., A p38alpha inhibitor containing a 4-benzylpiperidine motif, identified via a novel screening system in yeast. Mol Pharmacol. 2006;70(4 ): 1395-405.

Frost D, et al. beta-carboline compounds, including harmine, inhibit DYRK1A and tau phosphorylation at multiple Alzheimer's disease-related sites. PloS one. 2011 ;6(5):e19264.

Gallien S, et al. Large-Scale Targeted Proteomics Using Internal Standard Triggered-Parallel Reaction Monitoring (IS-PRM).Mol Cell Proteomics. 2015;14(6):1630-44.

Gandhi, et al. Activation of the aryl hydrocarbon receptor induces human type 1 regulatory T cell-like and Foxp3+ regulatory T cells. National Immunology, vol. 11, No. 9, 2010, pp. 846-853.

Georgievska B, et al. AZD1080, a novel GSK3 inhibitor, rescues synaptic plasticity deficits in rodent brain and exhibits peripheral target engagement in humans. J Neurochem.2013;125(3):446-56.

Georgopolos, et al. The Role of the Ikaros Gene in Lymphocyte Development And Homeostasis. Annu. Rev. Immunol, vol. 15, 1997, 155-76.

Ghofrani HA, et al. Imatinib in pulmonary arterial hypertension patients with inadequate response to established therapy. Am J Respir Grit Care Med. 2010;182(9):1171-7.

Gockler N, et al. Harmine specifically inhibits protein kinase DYRK1A and interferes with neurite formation. FEBS J. 2009;276(21):6324-37.

Goldberg SL, et al. An exploratory phase 2 study of investigational Aurora A kinase inhibitor alisertib (MLN8237) in acute myelogenous leukemia and myelodysplastic syndromes. Leuk Res Rep. 2014;3(2):58-61.

Gomberg-Maitland M, et al. A dosing/cross-development study of the multikinase inhibitor sorafenib in patients with pulmonary arterial hypertension. Clin Pharmacol Ther. 2010;87(3):303-10.

Gungor H, et al. Dose-finding quantitative FDG PET imaging study with the oral pan-AKT inhibitor GSK2141795 in patients with gynecological malignancies. J Nucl Med. 2015.

Han SK, et al. Enhancement of anti-inflammatory tendency by SB203580, p38alpha specific inhibitor, in human fibroblast-like synoviocyte cell line, MH7A. Rheumatology international. 2006;26(11):972-8.

Havasi A, et al., Histone acetyl transferase (HAT) HB01 and JADE1 in epithelial cell regeneration. Am J Pathol. 2013;182(1):152-62.

(56) References Cited

OTHER PUBLICATIONS

Hay AE, et al. A phase II study of AT9283, an aurora kinase inhibitor, in patients with relapsed or refractory multiple myeloma: NCIC clinical trials group IND.191. Leuk Lymphoma. 2015:1-4.

Hole S, et al., Aurora kinase A and B as new treatment targets in aromatase inhibitor-resistant breast cancer cells. Breast Cancer Res Treat. 2015; 149(3):715-26.

Holmes, et al. Peripheral natural killer cell maturation depends on the transcription factor Aiolos. The EMBO Journal, 33, 2014, pp. 2721-2734.

Hosokawa, et al. Human Aiolos, an Ikaros-Related Zinc Finger DNA Binding Protein: cDNA Cloning, Tissue Expression Pattern, and Chromosomal Mapping. Genomics, vol. 61, 1999, pp. 326-329.

Huang S, et al. Synthesis of 3-(1 H-benzimidazol-2-yl)-5-isoquinolin-4-ylpyrazolo[1,2-b]pyridine, a potent cyclin dependent kinase 1 (CDK1) inhibitor. Bioorg Med Chem Lett. 2007;17(5): 1243-5.

Hwang J, et al., SIRT1 negatively regulates the protein stability of HIPK2. Biochemical and biophysical research communications. 2013;441 (4):799-804.

Hynes J, et al. The discovery of (R)-2-(secbutylamino)-N-(2-methyl-5-(methylcarbamoyl)phenyl) thiazole-5-carboxamide (BMS-640994)—A potent and efficacious p38alpha MAP kinase inhibitor. Bioorg Med Chem Lett. 2008;18(6):1762-7.

International Search Report dated Mar. 6, 2017 for International Application No. PCT/US2016/061189.

Issinger OG. Casein kinases: pleiotropic mediators of cellular regulation. Pharmacol Ther. 1993;59(1): 1-30.

Jain M, et al., Rudhira/BCAS3 is a cytoskeletal protein that controls Cdc42 activation and directional cell migration during angiogenesis. Exp Cell Res.2012;318(6):753-67.

Jasinska-Stroschein M. et al., Concurrent rho-kinase and tyrosine kinase platelet-derived growth factor inhibition in experimental pulmonary hypertension. Pharmacology. 2014;93(3-4):145-50.

Jepsen K, and Rosenfeld MG. Biological roles and mechanistic actions of co-5 repressor complexes. J Cell Sci. 2002; 115(Pt.4):689-98.

Jin CH, et al. Ethyl 2-(benzylidene)-7-methyl-3-oxo-2,3-dihydro-5H-thiazolo[3,2-a]pyrimidine-6-carboxy late analogues as a new scaffold for protein kinase casein kinase 2 inhibitor. Bioorg Med Chem. 2014;22(17):4553-65.

Kalgutkar AS, et al. Preclinical pharmacokinetics and metabolism of 6-(4-(2, 5-difluorophenyl)oxazol-5-yl)-3-isopropyl-[1 ,2,4]-triazolo [4,3-a]pyridine, a novel and selective p38alpha inhibitor: identification of an active metabolite in preclinical species and human liver microsomes. Biopharm Drug Dispos. 2006;27(8):371-86.

Kelley, Helios, a novel dimerization partner of Ikaros expressed in the earliest hematopoietic progenitors. Current Biology, vol. 8, 1998, pp. 508-515.

Kelly KR, et al. Phase I study of MLN8237-investigational Aurora A kinase inhibitor—in relapsed/refractory multiple myeloma, non-Hodgkin lymphoma and chronic lymphocytic leukemia. Invest New Drugs. 2014;32(3):489-99.

Kikuchi, et al. Lacking of Aiolos accelerates pre-mature B cell apoptosis mediated by BCR signaling through elevation in cytochrome c release. Biochimica et Biophysica Acta, vol. 1793, 2009, pp. 1304-1314.

Kim, Ikaros DNA-Binding Proteins Direct Formation of Chromatin Remodeling Complexes in Lymphocytes. Immunity, vol. 10, 1999, pp. 345-355.

Kim R, et al. Triciribine Phosphate Monohydrate, an AKT Inhibitor, Enhances Gemcitabine Activity in Pancreatic Cancer Cells. Anticancer Res. 2015;35(9):4599-604.

Kioussis, et al. Aiolos: An Ungrateful Member of the Ikaros Family. Immunity, vol. 26, 2007, pp. 275-277.

Kirby LA, et al. Glycogen synthase kinase 3 (GSK3) inhibitor, SB-216763, promotes pluripotency in mouse embryonic stem cells. PloS one.2012;7(6):e39329.

Kissil JL, et al. Merlin, the product of the Nf2 tumor suppressor gene, is an inhibitor of the p21-activated kinase, Pak1. Mol Cell. 2003; 12(4):841-9.

Kohler J, et al. Lestaurtinib inhibits histone phosphorylation and androgen-dependent gene expression in prostate cancer cells. PloS one. 2012;7(4):e34973.

Kuglstatter A, et al. X-ray crystal structure of JNK2 complexed with the p38alpha inhibitor BIRB796: insights into the rational design of DFG-out binding MAP kinase inhibitors. Bioorg Med Chem Lett. 2010;20(17):5217-20.

Lali FV, et al. The pyridinyl imidazole inhibitor SB203580 blocks phosphoinositide-dependent protein kinase activity, protein kinase B phosphorylation, and retinoblastoma hyperphosphorylation in interleukin-2-stimulated T cells independently of p38 mitogen-activated protein kinase. The Journal of biological chemistry. 2000;275(10):7395-402.

Lara PN, Jr. et al. Phase II Study of the AKT Inhibitor MK-2206 plus Erlotinib in Patients with Advanced Non-Small Cell Lung Cancer Who Previously Progressed on Erlotinib. Clin Cancer Res. 2015;21 (19):4321-6.

Leivonen SK, et al. TGF-beta-elicited induction of tissue inhibitor of metalloproteinases (TIMP)-3 expression in fibroblasts involves complex interplay between Smad3, p38alpha, and ERK½. PloS one. 2013;8(2):e57474.

Li, et al. Aiolos Promotes Anchorage Independence by Silencing p66Shc Transcription in Cancer Cells. Cancer Cell, vol. 25, No. 5. 2014, pp. 575-589.

Li J, et al. A fluorescence-based assay for p38alpha recruitment site binders: identification of rooperol as a novel p38alpha kinase inhibitor. Chembiochem. 2013;14(1):66-71.

Li JP, et al. The investigational Aurora kinase A inhibitor alisertib (MLN8237) induces cell cycle G2/M arrest, apoptosis, and autophagy via p38 MAPK and Akt/mTOR signaling pathways in human breast cancer cells. Drug Des Devel Ther. 2015;9 (1627-52).

Licht, et al. From Anecdote to Targeted Therapy: The Curious Case of Thalidomide in Multiple Myeloma. Cancer Cell, vol. 25, No. 1, 2014, pp. 9-11.

Linding R, et al. NetworKIN: a resource for exploring cellular phosphorylation networks. Nucleic Acids Res. 2008;36(Database issue ):D695-9.

Linding R, et al. Systematic discovery of in vivo phosphorylation networks. Cell. 2007;129(7):1415-26.

Liu C, et al. Synthesis and evaluation of carbamoylmethylene linked prodrugs of BMS-582949, a clinical p38alpha inhibitor. Bioorg Med Chem Lett. 2013;23(10):3028-33.

Longo, et al., Letters to the editor. Haematologica 2014; 99:e122.

Ma BB, et al. Multicenter phase II study of the AKT inhibitor MK-2206 in recurrent or metastatic nasopharyngeal carcinoma from patients in the mayo phase II consortium and the cancer therapeutics research group (MC1 079). Invest New Drugs. 2015;33(4 ):985-91.

Ma, et al. Ikaros and Aiolos Inhibit Pre-B-Cell Proliferation by Directly Suppressing c-Myc Expression. Molecular and Cell Biology, vol. 30, No. 7, 2010, pp. 4149-4158.

Ma H, He Q, et al., Increased degradation of MYPT1 contributes to the development of tolerance to nitric oxide in porcine pulmonary artery. Am J Physiol Lung Cell Mol Physiol. 2010;299(1):L117-23.

Ma J, et al., Activation of JNK/c-Jun is required for the proliferation, survival, and angiogenesis induced by EET in pulmonary artery endothelial cells. J Lipid Res. 2012;53(6): 1093-105.

Ma, Y. et al., Aurora kinase inhibitor AZD1152 has an additional effect of platinum on a sequential application at the human ovarian cancer cell line SKOV3. Arch Gynecol Obstet. 2013;288(1):173-82.

Mancini M, et al. Gadd45a transcriptional induction elicited by the Aurora kinase inhibitor MK-0457 in Bcr-Abl-expressing cells is driven by Oct-1 transcription factor. Leuk Res. 2012;36(8):1028-34.

Mazur-Kolecka B, et al. Effect of DYRK1A activity inhibition on development of neuronal progenitors isolated from Ts65Dn mice. J Neurosci Res. 2012;90(5):999-1010.

Medarametla V, et al., PK10453, a nonselective platelet-derived growth factor receptor inhibitor, prevents the progression of pulmonary arterial hypertension. Pulm Circ. 2014; 4(1):82-102.

Melichar B, et al. Safety and activity of alisertib, an investigational aurora kinase A inhibitor, in patients with breast cancer, small-cell

(56) References Cited

OTHER PUBLICATIONS lung cancer, non-small-cell lung cancer, head and neck squamous-cell carcinoma, and gastro-oesophageal adenocarcinoma: a five-arm phase 2 study. Lancet Oncol. 2015;16(4):395-405.
Meyrick Bo, et al., Proteomics of transformed lymphocytes from a family with familial pulmonary arterial hypertension. Am J Respir Grit Care Med. 2008; 177(1):99-107.
Minatsuki S, et al. Platelet-derived growth factor receptor-tyrosine kinase inhibitor, imatinib, is effective for treating pulmonary hypertension induced by pulmonary tumor thrombotic microangiopathy. Int Heart J. 2015;56(2):245-8.
Miyagawa K, and Emoto N. A new class of drug for pulmonary arterial hypertension. Can a Rho-kinase inhibitor break the stagnation in treating it? Circ J. 2013;77(1 0):2477-8.
Moehren U, et al., Gene repression by nuclear 10 hormone receptors. Essays Biochem. 2004;40(89-104).
Montenarh M. Protein kinase CK2 and angiogenesis. Adv Clin Exp Med. 2014;23(2): 153-8.
Morecroft I, et al., Mice lacking the Raf-1 kinase inhibitor protein exhibit exaggerated hypoxia-induced pulmonary hypertension. Br J Pharmacol. 2011; 163(5):948-63.
Morgan, et al. Aiolos, a lymphoid restricted transcription factor that interacts with Ikaros to regulate lymphocyte differentiation. The EMBO Journal vol. 16, No. 8, 1997, pp. 2004-2013.
Morrell ED, et al., p38 mitogen-activated protein kinase mediates the sustained phase of hypoxic pulmonary vasoconstriction and plays a role in phase I vasodilation. J Surg Res. 2006;134(2):335-41.
Mortimer HJ, et al., p38 MAP kinase: essential role in hypoxia-mediated human pulmonary artery fibroblast proliferation. Pulm Pharmacol Ther.2007;20(6):718-25.
Mottis A, et al., Emerging roles of the corepressors NCoR1 and SMRT in homeostasis. Genes Dev.2013;27(8):819-35.
Murray BW, et al. Small-molecule p21-activated kinase inhibitor PF-3758309 is a potent inhibitor of oncogenic signaling and tumor growth. Proc Natl Acad Sci USA. 2010;107(20):9446-51.
Niu H, et al. Scientific Rationale Supporting the Clinical Development Strategy for the Investigational Aurora A Kinase Inhibitor Alisertib in Cancer. Front Oncol. 2015; 5(189).
Niu NK, et al. Pro-apoptotic and pro-autophagic effects of the Aurora kinase A inhibitor alisertib (MLN8237) on human osteosarcoma U-2 OS and MG-63 cells through the activation of mitochondria-mediated pathway and inhibition of p38 MAPKIPI3K/AkUmTOR signaling pathway. Drug Des Devel Ther. 2015;9(1555-84).
Norman, P., BMS-582949: crystalline form of a p38alpha inhibitor? WO2008079857. Expert Opin Ther Pat. Aug. 2009;19(8):1165-8. doi: 10.1517/13543770902816160.
Oki Y, et al. Phase II study of an AKT inhibitor MK2206 in patients with relapsed or refractory lymphoma. Br J Haematol. 2015.
Ostergaard L, et al., Pulmonary pressure reduction attenuates expression of proteins identified by lung proteomic profiling in pulmonary hypertensive rats. Proteomics. 2011;11(23):4492-502.
Pahud G, et al. Modulation of choline acetyltransferase synthesis by okadaic acid, a phosphatase inhibitor, and KN-62, a CaM kinase inhibitor, in NS-20Y neuroblastoma. Neurochem Int.2001 ;38 (1 ):75-82.
Perros, et al. Pulmonary Lymphoid Neogenesis in Idiopathic Pulmonary Arterial Hypertension. Americal Journal of Respiratory and Critical Care Medicing, vol. 185, 2012, pp. 311-321.
Phadke MS, et al. The Novel ATP-Competitive MEK/Aurora Kinase Inhibitor BI-847325 Overcomes Acquired BRAF Inhibitor Resistance through Suppression of Mcl-1 and MEK Expression. Mol Cancer Ther. 2015;14(6):1354-64.
Picotti P, et al. High-throughput generation of selected reaction-monitoring assays for proteins and proteomes. Nat Methods. 2010;7(1):43-6.
Praskova M, et al. Ca(2+)/calmodulin-dependent protein kinase (CaM-kinase) inhibitor KN-62 suppresses the activity of mitogen-activated protein kinase (MAPK), c-myc activation and human keratinocyte proliferation. Archives of dermatological research. 2002;294(4 ):198-202.
Qi L, and Zhang Y. Alisertib (MLN8237), a selective Aurora-A kinase inhibitor, induces apoptosis in human tongue squamous cell carcinoma cell both in vitro and in vivo. Tumour Biol. 2015;36(3):1797-802.
Qi W, et al. AT9283, a novel aurora kinase inhibitor, suppresses tumor growth in aggressive 8-celllymphomas. IntJ Cancer. 2012;130(12):2997-3005.
Qin J, et al. DC120, a novel AKT inhibitor, preferentially suppresses nasopharyngeal carcinoma cancer stem-like cells by downregulating Sox2. Oncotarget. 2015;6(9):6944-58.
Quintana, et al. Aiolos promotes TH17 differentiation by directly silencing //2 expression. National Immunology, vol. 13, No. 8, 2012, pp. 770-777.
Ramchandran R, et al., PKG-1 alpha leucine zipper domain defect increases pulmonary vascular tone: implications in hypoxic pulmonary hypertension. American journal of physiology Lung cellular and molecular physiology. 2014;307(7):L537-44.
Rauniyar, et al., Isobaric Labeling-based relative quantification in shotgun proteomics. Journal of proteome. 2014.13, 5293-5309.
Rebollo, et al. Ikaros, Aiolos and Helios: Transcription regulators and lymphoid malignancies. Immunology and Cell Biology, vol. 81, 2003, pp. 171-175.
Rosenthal, et al., A Phase Ib study of the combination of the Aurora Kinase inhibitor alisertib (MLN8237) and bortezomib in relapsed multiple myeloma. Br J Haematol. 2015.
Ruben K, et al. Selectivity Profiling and Biological Activity of Novel beta-Carbolines as Potent and Selective DYRK1 Kinase Inhibitors. PloS one. 2015; 10(7):e0132453.
Ryu BJ, et al. PF-3758309, p21-activated kinase 4 inhibitor, suppresses migration and invasion of A549 human lung cancer cells via regulation of CREB, NF-kappaB, and beta-catenin signalings. Mol Cell Biochem. 2014;389(1-2):69-77.
Safaei J, et al. Prediction of 492 human protein kinase substrate specificities. Proteome Sci. 2011 ;9 Suppl 1 (S6).
Sakao S, and Tatsumi K. Vascular remodeling in pulmonary arterial hypertension: multiple cancer-like pathways and possible treatment modalities. Int J Cardiol. 2011; 147(1):4-12.
Sakao S, et al., Reversible or irreversible remodeling in pulmonary arterial hypertension. Am J Respir Cell Mol Biol. 2010;43(6):629-34.
Saveanu C, et al. The p21-activated protein kinase inhibitor Skb15 and its budding yeast homologue are 60S ribosome assembly factors. Mol Cell Bioi.2007;27(8):2897-909.
Scaglioni PP, et al., A CK2-dependent mechanism for degradation of the PML tumor suppressor. Cell. 2006; 126(2):269-83.
Scaglioni PP, et al., CK2 mediates phosphorylation and ubiquitin-mediated degradation of the PML tumor suppressor. Mol Cell Biochem. 2008;316(1-2):149-54.
Schmitt C, et al. Design and synthesis of a library of lead-like 2,4-bisheterocyclic substituted thiophenes as selective Dyrk/Cik inhibitors. PloS one. 2014;9(3):e87851.
Schmitt C, et al. Hydroxybenzothiophene Ketones Are Efficient Pre-mRNA Splicing Modulators Due to Dual Inhibition of Dyrk1A and Clk1/4. ACS Med Chem Lett. 2014;5(9):963-7.
Schwappacher R, et al. A molecular mechanism for therapeutic effects of cGMP-elevating agents in pulmonary arterial hypertension. J Biol Chem.2013;288(23):16557-66.
Sisask G, et al. Rats treated with AZD2858, a GSK3 inhibitor, heal fractures rapidly without endochondral bone formation. Bone. 2013;54(1): 126-32.
Sitz JH, et al. The Down syndrome candidate dual-specificity tyrosine phosphorylation-regulated kinase 1A phosphorylates the neurodegeneration-related septin 4. Neuroscience. 2008; 157(3):596-605.
Soderblom EJ, et al. Quantitative label-free phosphoproteomics strategy for multifaceted experimental designs. Anal Chem. 2011 ;83(10):3758-64.
Stahl S, et al., Phosphoproteomic profiling of NSCLC cells reveals that ephrin B3 regulates pro-survival signaling through Akt1-mediated phosphorylation of the EphA2 receptor. J Proteome Res. 2011; 10(5):2566-78.

(56) References Cited

OTHER PUBLICATIONS

Sun, et al. Lack of the Transcriptional Coactivator OBF-1 Prevents the Development of Systemic Lupus Erythematosus-Like Phenotypes in Aiolos Mutant Mice. Journal of Immunology, vol. 170, 2003, pp. 1699-1706.

Take Y, et al. DNA-10 dependent protein kinase inhibitor (OK-1035) suppresses p21 expression in HCT116 cells containing wild-type p53 induced by adriamycin. Biochemical and biophysical research communications. 1996;221 (2):207-12.

Take Y, et al. OK-1035, a selective inhibitor of DNA-dependent protein kinase. Biochemical and biophysical research communications. 1995;215(1):41-7.

Ten Freyhaus H, et al. Hypoxia enhances platelet-derived growth factor signaling in the pulmonary vasculature by down-regulation of protein tyrosine phosphatases. Am J Respir Grit Care Med. 2011;183(8):1092-102.

Tibes R, et al. Phase I study of the novel Cdc2/CDK1 and AKT inhibitor terameprocol in patients with advanced leukemias. Invest New Drugs. 2015; 33(2):389-96.

Timmermann S, et al., Histone acetylation and disease. Cell Mol Life Sci. 2001 ;58(5-6):728-36.

To K, et al. The phosphoinositide-dependent kinase-1 inhibitor 2-amino-N-[4-[5-(2-phenanthrenyl)-3-(trifluoromethyl)-1H-pyrazol-1-yl]phenyl]-ace tamide (OSU-03012) prevents Y-box binding protein-1 from inducing epidermal growth factor receptor. Mol Pharmacol. 2007;72(3):641-52.

Tombes RM, et al. G1 cell cycle arrest and apoptosis are induced in NIH 3T3 cells by KN-93, an inhibitor of CaMK-11 (the multifunctional Ca2+/CaM kinase). Cell Growth Differ. 1995;6(9):1063-70.

Tseng PH, et al. Overcoming trastuzumab resistance in HER2-overexpressing breast cancer cells by using a novel celecoxib-derived phosphoinositide-dependent kinase-1 inhibitor. Mol Pharmacol. 2006;70(5):1534-41.

Tseng PH, et al. Synergistic interactions between imatinib mesylate and the novel phosphoinositide-dependent kinase-1 inhibitor OSU-03012 in overcoming imatinib mesylate resistance. Blood.2005; 105(10):4021-7.

Tsuboi K, et al. A Phase I study to assess the safety, pharmacokinetics and efficacy of barasertib (AZD1152), an Aurora B kinase inhibitor, in Japanese patients with advanced acute myeloid leukemia. Leuk Res. 2011;35(10): 1384-9.

Tuder, et al. Plexiform lesion in severe pulmonary hypertension: association with glomeruloid lesion. Am J Pathol. Jul. 2001;159(1):382-3.

Tuder RM, Groves B, Badesch DB, and Voelkel NF. Exuberant endothelial cell growth and elements of inflammation are present in plexiform lesions of pulmonary hypertension. Am J Pathol. 1994;144(2):275-85.

Venkatakrishnan K, et al. Phase 1 study of the investigational Aurora A kinase inhibitor alisertib (MLN8237) in East Asian cancer patients: pharmacokinetics and recommended phase 2 dose. Invest New Drugs.2015; 33(4):942-53.

Veuger SJ, et al. Radiosensitization and DNA repair inhibition by the combined use of novel 15 inhibitors of DNA-dependent protein kinase and poly(ADP-ribose) polymerase-1. Cancer Res. 2003;63(18):6008-15.

Vigneron C, et al. Effect of roscovitine, a cdk1 inhibitor, and of the presence of oocyte on bovine cumulus cell expansion and cyclooxygenase-2 expression. Mol 50 Reprod Dev. 2003;65(1):114-21.

Villa, et al. Reversible Pulmonary Hypertension Related to Thalidomide Treatment for Multiple Myeloma. Case Reports in Oncology, vol. 4, 2011, pp. 487-489.

Wang, et al. Overexpression of Aiolos in Nalm-6 acute lymphoblastic leukaemia cells reduces apoptosis by suppressing phosphatase and tensin homologue deleted on chromosome 10 and activating the phosphatidylinositol-3-kinase/Akt signalling pathway. Molecular Medicine Reports. vol. 11, 2015, pp. 457-3464.

Welsh DJ, et al., p38 MAP kinase isoform activity and cell cycle regulators in the proliferative response of pulmonary and systemic artery fibroblasts to acute hypoxia. Pulm Pharmacol Ther. 2006;19(2):128-38.

Weng SC, et al. Sensitizing estrogen receptor-negative breast cancer cells to tamoxifen with OSU-03012, a novel celecoxib-derived phosphoinositide-dependent protein kinase-1/Akt signaling inhibitor. Mol Cancer Ther.2008;7(4):800-8.

Wilson, et al. Hyperplastic Growth of Pulmonary Artery Smooth Muscle Cells from Subjects with Pulmonary Arterial Hypertension Is Activated through JNK and p38 MAPK. Plos One, Apr. 23, 2015, pp. 1-16.

Xia Q, et al. The CDK1 inhibitor R03306 improves the response of BRCA-proficient breast cancer cells to PARP inhibition. Int J Oncol. 2014;44(3):735-44.

Yu L, et al., Cyclin-dependent kinase inhibitor p27Kip1, but not p21WAF1/Cip1, is required for inhibition of hypoxia-induced pulmonary hypertension and remodeling by heparin in mice. Circ Res.2005;97(9):937-45.

Zhang, et al. BMP4 Increases the Expression of TRPC and Basal [Ca2+]i via the p38MAPK and ERK1/2 Pathways Independent of BMPRII in PASMCs. Plos One, 2014, pp. 1-16.

Zhang J, et al. LCH-7749944, a novel and potent p21-activated kinase 4 inhibitor, suppresses proliferation and invasion in human gastric cancer cells. Cancer Lett. 2012;317(1):24-32.

Zhang X, et al. Identifying novel targets of oncogenic EGF receptor signaling in lung cancer through global phosphoproteomics. Proteomics. 2015; 15(2-3):340-55.

Zhu J, et al. From the cyclooxygenase-2 inhibitor celecoxib to a novel class of 3-phosphoinositide-dependent protein kinase-1 inhibitors. Cancer Res. 2004;64(12):4309-18.

Zhuang, et al. Matura Overexpression of AIOLOS inhibits cell proliferation and suppresses apoptosis in Nalm-6 cells. Oncology Reports, vol. 31, 2014, 1183-1190.

Zhuang, et al. Upregulation of AIOLOS induces apoptosis and enhances etoposide chemosensitivity in Jurkat leukemia cells. Oncology Reports, vol. 33, 2015, pp. 1319-1325.

Zullo KM, Guo Y, et al. Aurora A Kinase Inhibition Selectively Synergizes with Histone Deacetylase Inhibitor through Cytokinesis Failure in T-cell Lymphoma. Clin Cancer Res. 2015;21 (18):4097-109.

\* cited by examiner

A

B

METHODS OF DETECTING AND TREATING PULMONARY HYPERTENSION

CROSS REFERENCE

This Application is a continuation of U.S. patent application Ser. No. 16/421,099 filed May 23, 2019, which is a continuation of U.S. patent application Ser. No. 15/347,439 filed Nov. 9, 2016, which claims the benefit of U.S. Provisional Application No. 62/253,184, filed Nov. 10, 2015, the contents of which are incorporated herein by reference in their entirety.

GOVERNMENT RIGHTS

The invention was made with government support under R03HL110821 awarded by the National Heart, Lung, and Blood Institute (NHLBI). The government has certain rights in the invention.

The instant application contains a Sequence listing which has been submitted electronically in ASCII format and is hereby incorporated by reference in its entirety. Said ASCII copy, created Feb. 7, 2020, is named SequenceListing.txt and is 30,830 bytes in size.

BACKGROUND

Pulmonary hypertension (PH) is a rare disorder of the pulmonary vasculature that is associated with high morbidity and mortality. The pathology of the disease includes plexiform lesions of disorganized angiogenesis and abnormal neointimal cellular proliferation, which obstruct blood flow through the pulmonary arterioles. Phosphorylation patterns of proteins occur at various stages of PH.

INCORPORATION BY REFERENCE

Each patent, publication, and non-patent literature cited in the application is hereby incorporated by reference in its entirety as if each was incorporated by reference individually.

SUMMARY OF THE INVENTION

In some embodiments, the invention provides a method comprising: a) adding to a sample of a protein extracted from a buffy coat an amount of a quantification standard to provide a test sample; and b) assaying the test sample to quantify in the test sample a wild type phosphopeptide of the protein extracted from the buffy coat, wherein the quantifying is based on the amount of the quantification standard, wherein the quantification standard is a form of the phosphopeptide that is isotopically enriched to a non-natural abundance of an isotope.

In some embodiments, the invention provides a chemical aliquot comprising a sample of a phosphopeptide, wherein at least 1% of the sample of the phosphopeptide consists of molecules that have an amino acid residue that has at least two $^{13}C$ nuclei, wherein the sample contains at least 1 pg of the phosphopeptide, wherein the phosphopeptide has at least 90% sequence identity to any compound of any of TABLE 2 or TABLE 3.

In some embodiments, the invention provides a kit comprising: a) a chemical aliquot comprising a sample of a phosphopeptide, wherein at least 1% of the sample of the phosphopeptide consists of molecules that have an amino acid residue that has at least two $^{13}C$ nuclei, wherein the sample contains at least 1 pg of the phosphopeptide, wherein the phosphopeptide has at least 90% sequence identity to any compound of any of TABLE 2 or TABLE 3; and b) an additional aliquot comprising a sample of the phosphopeptide that has nuclei in a natural abundance of isotopes.

DETAILED DESCRIPTION

Figure 1:
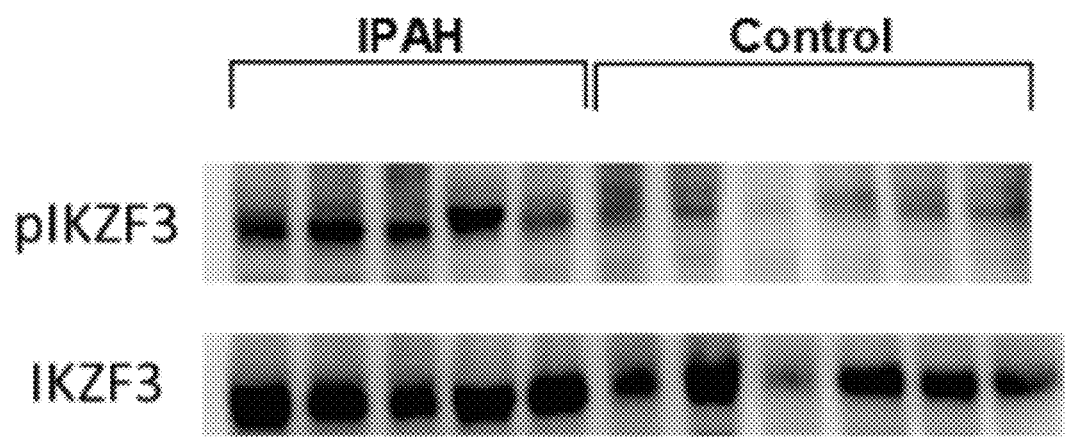
FIG. 1 shows western blots with phospho-specific and total IKZF3 antibodies.
Figure 1:
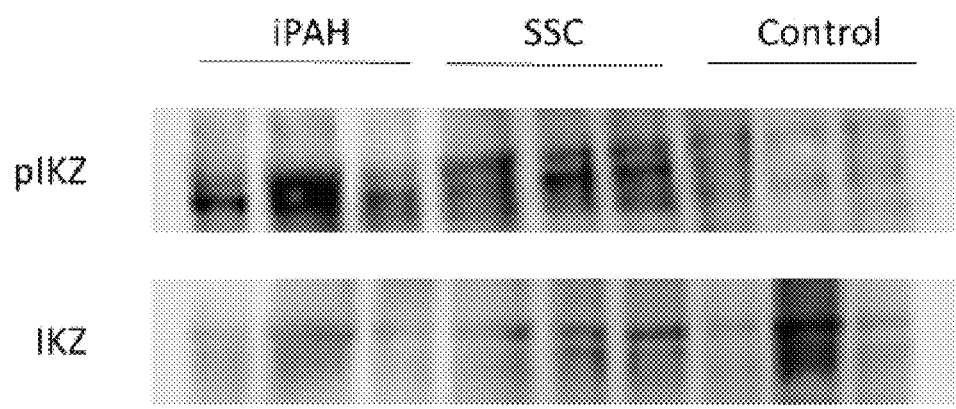

Pulmonary hypertension (PH), or pulmonary arterial hypertension (PAH), is a chronic disease that affects the arteries in the lungs and the right side of the heart. If left untreated, PAH can lead to heart failure; thus, PAH is a disorder associated with high morbidity and mortality. The World Health Organization (WHO) classifies PH into five groups based on the underlying associated disease: Group 1: PAH, Group 2: PH due to left heart disease, Group 3: PH due to lung disease or hypoxia, Group 4: chronic thromboembolic PH (CTEPH), and Group 5: PH resulting from unclear multifactorial mechanisms.

Subjects with PAH include those with idiopathic (iPAH) or heritable PAH associated with genetic mutations in the bone morphogenic type 2 receptor (BMPR2), activin-like kinase type 1 (ALK-1), endoglin (ENG), SMAD family member 9 (SMAD9), caveolin 1 (CAV1), or potassium two pore domain channel subfamily K member 3 (KCNK3). PAH can also be associated with connective tissue disease (e.g., systemic sclerosis (scleroderma), mixed connective tissue disease, or other autoimmune disorders), human immunodeficiency virus (HIV) infection, portal hypertension, congenital heart diseases, schistosomiasis, pulmonary veno-occlusive disease, pulmonary capillary hemangiomatosis, or persistent pulmonary hypertension of the newborn (PPHN). Response to therapy is variable for subjects with PAH.

The pathology of PAH includes complex vascular formations resulting from the remodeling of pulmonary arteries called plexiform lesions (PLs) and abnormal neointimal cellular proliferation, which obstruct blood flow through the pulmonary arterioles. Kinases play a critical role in cell growth and proliferation and can be targeted to address the underlying pathology of PAH. Kinase inhibitors can be used to treat PAH upon detecting the phosphorylation of proteins involved in the pathology of PAH.

Biomarkers that indicate the pathologic mechanism, severity of the disease, and treatment response can identify subjects who require more aggressive therapeutic interventions or alternative treatments. Biomarkers can also be used to identify subjects who are more likely to respond to kinase inhibitors for the treatment of PAH.

Biomarkers for the Detection and Treatment of Pulmonary Arterial Hypertension

The disclosed invention describes a method of determining the status of diagnoses and prognoses of PAH in subjects by quantifying increases or decreases in the phosphorylation (i.e., phosphorylation profile") of a subset of proteins. The invention describes a method of determining the phosphorylation level of one or more proteins using tissue samples of subjects with PAH. In some embodiments, the invention determines the phosphorylation level of one or more proteins using tissue samples of subjects with idiopathic PAH (iPAH). The disclosed invention compares the phosphorylation level of proteins in a sample to the phosphorylation level of the corresponding proteins in at least one control. In some embodiments, the control is a sample obtained from a subject diagnosed with PAH. In some embodiments, the control is a sample obtained from a subject diagnosed with iPAH. In some embodiments, the control is a sample obtained from a subject free of pathology.

The disclosed invention can use analytical methods to determine the relative abundance of phosphorylated proteins in PAH subjects. An increase or decrease in phosphorylation of proteins (i.e., phosphoproteins) compared to the phosphorylation levels of control samples can suggest a disease state.

The disclosed invention can identify PAH by detecting an increase in phosphorylation of at least one protein of TABLE 2. For example, the method can detect increased phosphorylation of at least one of: Ikaros family zinc finger protein 3 (IKZF3), histocompatibility (minor) antigen HA-1 (HMHA1), breast carcinoma amplified sequence 3 (BCAS3), rho-GTPase-activating protein 25 (RHG25), nuclear mitotic apparatus protein 1 (NUMA1), leukosialin (LEUK), mucin 1-cell surface associated protein (MUC1), nuclear pore complex protein Nup214 (NU214), WD repeat-containing protein 24 (WDR24), aquarius intron-binding spliceosomal factor (AQR), 1A69, apoptosis-stimulating protein of p53 1 (ASPP1), mitogen-activated protein kinase (MK14), zinc finger protein 404 (ZN404), oxysterol-binding protein (OSB11), and hepatoma-derived growth factor (HDGF). In some embodiments, the method can detect increased phosphorylation of IKZF3, HMHA1, BCAS3, RHG25, NUMA1, ZN404, and HDGF.

IKZF3 functions as an epigenetic driver of lymphocyte mimicry in metastatic epithelial cancers and plays a key role in B cell malignancies, including multiple myeloma (MM). Ikaros family zinc finger protein 1 (IKZF1) and IKZF3 are transcription factors that are essential for MM growth. Thalidomide and other drugs used for the treatment of MM bind to cereblon, a component of a ubiquitin ligase complex, and alter the specificity of the complex to induce the ubiquitination and degradation of IKZF1 and IKZF3. The phenotype of IKZF3 knockout mice is similar to that of systemic lupus erythematosus (SLE), which can cause PH.

RHG25 is a GTPase activator for Rho-type GTPases, and acts by converting Rho-type GTPases into inactive GDP-bound states. Rho-GTPases affect actin organization, cell shape, and cell spreading, and thus regulate the cytoskeleton and maintain endothelial barrier function. Cytoskeletal defects are common in the presence of multiple BMPR2 mutations and are associated with activation of the Rho-GTPase RAC1. Differences in Rho-GTPase gene expression can be observed in cultured lymphocytes between samples obtained from vasodilator reactive and non-vasodilator reactive PAH subjects.

HMHA1 is a GTPase activator for Rho-type GTPases. HMHA1 co-localizes with the Rho-GTPase Rac1. HMHA1 is expressed in hematopoietic, epithelial tumor, and endothelial cells.

NUMA1 is a component of the nuclear matrix and serves a non-mitotic structural role. NUMA1 interacts with microtubules and plays a role in the formation and organization of the mitotic spindle during cell division. NUMA1 also functions as a tether that links bulk microtubules of the spindle to centrosomes, and is required for proper alignment of the mitotic spindle during asymmetric cell divisions.

ASPP1 binds p53 and stimulates apoptotic effects. ASPP plays a role in stabilizing hematopoietic stem cells and is necessary for lymphatic vessel formation. ASPP1 also induces apoptosis independently of p53. By binding to p63 and p73 in vitro and in vivo, ASPP1 stimulates the transactivation function of p63 and p73 on the promoters of Bax, PIG3, and PUMA, but not MDM2 or $p21^{WAF-1/CIP1}$.

HDGF is a DNA-binding nuclear factor that can cause abnormal cell proliferation, increase the expression of vascular endothelial growth factor (VEGF), and lead to angiogenesis. Dephosphorylation of HDGF can lead to endothelial cell apoptosis. HDGF can also activate the PI3K/AKT pathway.

In one embodiment, the sample phosphorylation profile of a sample comprises the phosphorylation level of IKZF3. In some embodiments, the sample phosphorylation profile of a sample comprises the phosphorylation level of IKZF3, wherein IKZF3 is phosphorylated at amino acid S378. In some embodiments, phosphorylation of IKZF3 is upregulated in PAH samples.

In one embodiment, the sample phosphorylation profile comprises the phosphorylation level of RHG25. In some embodiments, the sample phosphorylation profile comprises the phosphorylation level of RHG25, wherein RHG25 is phosphorylated at amino acid T442. In one embodiment, the sample phosphorylation profile comprises the phosphorylation level of HMHA1. In some embodiments, the sample phosphorylation profile comprises the phosphorylation level of HMHA1, wherein HMHA1 is phosphorylated at amino acid S73.

In some embodiments, the sample phosphorylation profile comprises the phosphorylation level of NUMA1, wherein NUMA1 is phosphorylated at amino acids S2047 or S1969. In some embodiments, the sample phosphorylation profile comprises the phosphorylation level of NUMA1, wherein NUMA1 is phosphorylated at amino acids S2047 and S1969. In one embodiment, the sample phosphorylation profile comprises the phosphorylation level of ASPP1. In some embodiments, the sample phosphorylation profile comprises the phosphorylation level of ASPP1, wherein ASPP1 is phosphorylated at amino acid S710.

In one embodiment, the sample phosphorylation profile comprises the phosphorylation level of HDGF. In some embodiments, the sample phosphorylation profile comprises the phosphorylation level of HDGF, wherein HDGF is phosphorylated at amino acid S107.

In one embodiment, the sample phosphorylation profile comprises the phosphorylation level of NCOR1. In some embodiments, the sample phosphorylation profile comprises the phosphorylation level of NCOR1, wherein NCOR1 is phosphorylated at amino acid S999. In one embodiment, the sample phosphorylation profile comprises the phosphorylation level of BCAS3. In some embodiments, the sample phosphorylation profile comprises the phosphorylation level of BCAS3, wherein BCAS3 is phosphorylated at amino acid S709.

In some embodiments, the disclosed invention can diagnose PAH by detecting a decrease in phosphorylation. In some embodiments, the method can detect decreased phosphorylation of at least one of the proteins of TABLE 3: protein tyrosine phosphatase receptor type B (PTPRB), putative synaptogyrin-2 like protein (SNGL2), HIV Tat-specific factor 1 (HTSF1), PC3 and SFRS1-interacting protein (PSIP), Annexin A2 (ANXA2), S10A9, RLA2, TM100, serine/arginine-rich splicing factor 2 (SRSF2), phospholipase D1 (PLD1), brain-specific angiogenesis inhibitor 1-associated protein 2-like protein 2 (BI2L2), TENS1, microtubule associated protein 1B (MAP1B), or catenin alpha-1 (CTNA1).

PTPRB plays an important role in blood vessel remodeling and angiogenesis. PTPRB is not necessary for the initial formation of blood vessels, but is essential for maintaining and remodeling blood vessels. In pulmonary arteries, hypoxia of smooth muscle cells (SMCs) decreases expression of several PTPs, including T cell protein tyrosine phosphatase (PTP), density-enhanced phosphatase-1, PTP1B, and SH2 domain-containing phosphatase-2, which reduce PTP activity. Hypoxia-inducible factor (HIF)-1-alpha is involved in regulating gene expression because HIF-1-alpha siRNA abolished hypoxia-induced PDGFRbeta hyperphosphorylation and PTP downregulation. PDGFRbeta hyperphosphorylation and PTP downregulation are also present in vivo in mice with chronic hypoxia-induced PH.

Histone deacetylases (HDACs) are implicated in proliferation and adventitial fibroblasts in PAH. Phosphorylation of HDAC2 is mediated by casein kinase 2 (CK2alpha). Serine phosphorylation of HDAC2 is required for subsequent acetylation of HDAC2, and serine phosphorylation of HDAC2 decreases the deacetylase activity of HDAC2. Serine phosphorylation increases interactions with transcription co-repressors, such as SAP30, RBAp46/48, MDB3, and HDAC1, as well as interactions with p65 and p53.

In some embodiments, increased phosphorylation is detected, for example, in at least 1, 2, 3, 4, 5, 6, 7, 8, 9, or 10 proteins in TABLE 2. In some embodiments, decreased phosphorylation is detected, for example, in at least 1, 2, 3, 4, 5, 6, 7, 8, 9, or 10 proteins in TABLE 3.

In some embodiments, administration of an agent increases phosphorylation in at least 1, 2, 5, or 10 proteins in TABLE 2. In some embodiments, administration of an agent increases phosphorylation in at least 1 protein in TABLE 2. In some embodiments, administration of an agent increases the phosphorylation in at least 5 proteins in TABLE 2.

In some embodiments, administration of an agent decreases phosphorylation in at least 1, 2, 5, or 10 proteins in TABLE 3. In some embodiments, administration of an agent decreases phosphorylation in at least 1 protein in TABLE 3. In some embodiments, administration of an agent decreases phosphorylation in at least 5 proteins in TABLE 3.

In some embodiments, the agent is an inhibitor of CK2, CDK1, MAPK, PRK, AKT1, AurkA, CamK2B, CAMK4, GSK3A, GSK3B, HIPK2, HYRC, PDK, DYRK2, or PAK. In some embodiments, the agent is an inhibitor of CK2. In some embodiments, the agent is an inhibitor of CDK1. In some embodiments, the agent is TBB (4,5,6,7-tetrabromo-1-H-benzotriazole).

In some embodiments, the administration of an agent inhibits phosphorylation of NUMA1 at S2047. In some embodiments, administration of an agent inhibits phosphorylation of NUMA1 at S1969. In some embodiments, the agent inhibits phosphorylation of NCOR1 at S999. In some embodiments, administration of an agent inhibits phosphorylation of HDGF at S107. In some embodiments, an agent decreases or inhibits the phosphorylation of HMHA1 at S73. In some embodiments, an agent decreases or inhibits phosphorylation of ASPP1 at S710.

In some embodiments, the agent is a compound of the formula:

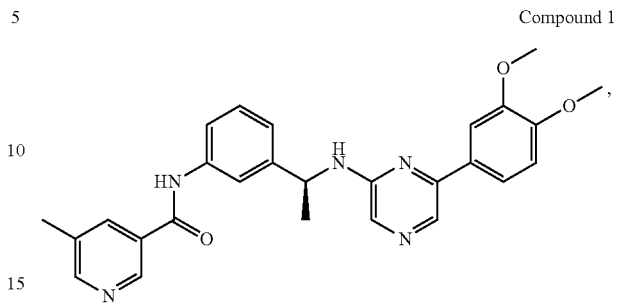

Compound 1 or a pharmaceutically-acceptable salt thereof. A pharmaceutically-acceptable salt can arise from the addition of an acid to a compound of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccharic acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid. In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccharate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

Samples Used to Determine Phosphorylation Levels of Proteins

The disclosed invention can quantify changes in phosphopeptides by obtaining a sample from a human subject. In some embodiments, the sample to be tested can be lung tissue, blood, whole blood, plasma, serum, circulating cells, peripheral blood mononuclear cells (PMBCs), or a lung biopsy. In some embodiments, samples can be obtained from circulating cells, such as cells in the buffy coat isolated in a Ficoll gradient, lymphocytes or subtypes of lymphocytes (i.e., T cells, B cells, or other subtypes of T and B cells), or circulating progenitor cells (i.e., progenitor endothelial cells, fibroblasts, or stem cells). Buffy coat samples include white blood cells (leukocytes), platelets, PMBCs, lymphocytes (T cells, B cells, and NK cells), and monocytes. In some embodiments, samples can be cells isolated from a subject and grown in cell culture or transformed or immortalized. In some embodiments, samples can be cells grown using conventional cell culture methods.

Samples can be placed in a phosphatase inhibitor cocktail containing various phosphatase inhibitors and protease inhibitors to prevent dephosphorylation during sample processing. Proteins can be extracted using homogenization, sonication in radioimmunoprecipitation assay (RIPA) lysis buffer, or sonication in denaturing buffers containing detergents and inhibitors to preserve the phosphorylation state of the proteins.

Extracted, isolated proteins can be digested using proteolytic enzymes. In some embodiments, proteins are digested using LysC or trypsin. In some embodiments, proteins are digested using proteolytic enzymes and purified by column chromatography. In some embodiments, proteins are digested using proteolytic enzymes and purified using Sep-PAK cartridges or using high performance liquid chromatography (HPLC). In some embodiments, proteins are extracted using organic solvents, for example, methylene chloride, chloroform, ethyl acetate, or acetonitrile.

Isotopically-Enriched Peptides for Use as Internal Standards

In some embodiments, the amount of phosphoproteins in a sample can be compared to an amount of stable, isotopically-enriched internal standards of phosphopeptides that are upregulated or downregulated in PAH. A set of stable, isotopically-enriched peptides can be used, for example, in a parallel reaction monitoring (PRM) mass spectroscopy (PRM-MS) assay to quantify the level of target phosphoproteins.

The digested test samples can be spiked with an amount of an isotopically-enriched standard to quantify amounts of phosphopeptides. The invention can quantify the amount of wild type phosphopeptide by comparing the amount of wild type phosphopeptide in a sample to the amount of an internal standard. In some embodiments, the internal standard is an isotopically-enriched peptide of a non-phosphorylated wild type peptide. In some embodiments, the internal standard is an isotopically-enriched peptide of a phosphorylated wild type peptide.

The peptides of the invention that are used as internal standards can be enriched with stable isotopes. In some embodiments, the peptides of the invention can be labeled with $^{13}C$, $^{15}N$, $^{18}O$, $^{32}P$, or any combination thereof. In some embodiments, the peptides of the invention are labeled with $^{13}C$. In some embodiments, the peptides of the invention are labeled with $^{15}N$. In some embodiments, the peptides of the invention are labeled with $^{13}C$ and $^{15}N$.

Stable, isotopically-enriched peptides of the invention include stable, isotopically-enriched peptides of TABLE 2 or TABLE 3. In some embodiments, the stable, isotopically-enriched peptides of the invention are peptides of TABLE 6 and TABLE 7. The stable, isotopically-enriched peptides of the invention can be phosphorylated or non-phosphorylated. In some embodiments, the stable, isotopically-enriched peptides of the invention have 1, 2, 3, 4, or 5 phosphorylated amino acids. In some embodiments, the stable, isotopically-enriched peptides of the invention have 1 phosphorylated amino acid. In some embodiments, the stable, isotopically-enriched peptides of the invention have 2 phosphorylated amino acids.

The peptides of the invention can comprise isotopically-enriched residues of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine. In some embodiments, the peptides of the invention comprise isotopically-enriched lysine. In some embodiments, the peptides of the invention comprise isotopically-enriched arginine. In some embodiments, the peptides of the invention comprise isotopically-enriched lysine and arginine.

The isotopically-enriched peptides of the invention can have 1, 2, 3, 4, 5, 6, 7, 8, 9, 10, 11, 12, 13, 14, 15, 16, 17, 18, 19, or 20 stable isotopes. In some embodiments, the isotopically-enriched peptides of the invention have 6 stable isotopes. In some embodiments, the isotopically-enriched peptides of the invention have 8 stable isotopes. In some embodiments, the isotopically-enriched peptides of the invention have 10 stable isotopes. In some embodiments, the isotopically-enriched peptides of the invention have at least 2 $^{13}C$ nuclei. In some embodiments, the isotopically-enriched peptides of the invention have at least 5 $^{13}C$ nuclei. In some embodiments, the isotopically-enriched peptides of the invention have at least 2 $^{15}N$ nuclei.

The peptides of the invention can comprise 1, 2, 3, 4, 5, 6, 7, 8, 9, or 10 isotopically-enriched amino acid residues. In some embodiments, the peptides of the invention can comprise 1 isotopically-enriched amino acid residue. In some embodiments, the peptides of the invention can comprise 2 isotopically-enriched amino acid residues.

The isotopically-enriched peptides of the invention can share a degree of homology with the wild type peptides. A pair of wild type and isotopically-enriched peptides can have, for example, up to about 20% pairwise homology, up to about 25% pairwise homology, up to about 30% pairwise homology, up to about 35% pairwise homology, up to about 40% pairwise homology, up to about 45% pairwise homology, up to about 50% pairwise homology, up to about 55% pairwise homology, up to about 60% pairwise homology, up to about 65% pairwise homology, up to about 70% pairwise homology, up to about 75% pairwise homology, up to about 80% pairwise homology, up to about 85% pairwise homology, up to about 90% pairwise homology, up to about 95% pairwise homology, up to about 96% pairwise homology, up to about 97% pairwise homology, up to about 98% pairwise homology, up to about 99% pairwise homology, up to about 99.5% pairwise homology, or up to about 99.9% pairwise homology.

A pair of wild type and isotopically-enriched peptides can have, for example, at least about 20% pairwise homology, at least about 25% pairwise homology, at least about 30% pairwise homology, at least about 35% pairwise homology, at least about 40% pairwise homology, at least about 45% pairwise homology, at least about 50% pairwise homology, at least about 55% pairwise homology, at least about 60% pairwise homology, at least about 65% pairwise homology, at least about 70% pairwise homology, at least about 75% pairwise homology, at least about 80% pairwise homology, at least about 85% pairwise homology, at least about 90% pairwise homology, at least about 95% pairwise homology, at least about 96% pairwise homology, at least about 97% pairwise homology, at least about 98% pairwise homology, at least about 99% pairwise homology, at least about 99.5% pairwise homology, at least about 99.9% pairwise homology.

Various methods and software programs can be used to determine the homology between two or more peptides, such as NCBI BLAST, Clustal W, MAFFT, Clustal Omega, AlignMe, Praline, or another suitable method or algorithm.

Analytical Methods to Determine Phosphorylation Levels of Proteins

The disclosed invention can quantify phosphorylation levels of proteins of a test sample using various analytical methods. Phosphorylation levels of proteins of a test sample can be detected using MS, for example, PRM-MS. In some embodiments, the mass spectrometer is tuned to detect that the native protein has a different m/z ratio compared to the isotopically-enriched peptides of the invention.

Phosphorylation levels of proteins of a test sample can also be determined using HPLC/MS/MS methods, phospho-specific antibodies, western blotting or enzyme-linked immunosorbent assays (ELISAs) that use antibodies specific to phosphorylated peptides or regions of a protein, chemiluminsecence, colorimetric detection methods, or horseradish peroxidase (HRP). Phosphorylation levels of proteins of a test sample can be determined by arranging proteins in arrays and analyzing the samples using flow cytometry or by plating proteins on slides for detection.

Kits for Detecting Pulmonary Hypertension

The disclosed invention also describes a kit comprising a chemical aliquot comprising a sample of an isotopically-enriched phosphopeptide that can be used to quantify phosphorylation levels of proteins in a test sample. The chemical aliquots can contain isotopically-enriched internal standards of a set of phosphopeptides. In some embodiments, a set of stable, isotopically-enriched peptides can be used to quantify amounts of phosphopeptides by PRM-MS. In some embodiments, the kit comprises unlabeled wild type peptides that are used to generate MS calibration curves.

In some embodiments, the kit comprises unlabeled, wild type peptides that can be used to generate MS calibration curves. In some embodiments, the kit can contain 4 variations of a peptide A: wild type phosphopeptide A, wild type non-phosphorylated peptide A, isotopically-enriched phosphopeptide A, and isotopically-enriched non-phosphorylated peptide A. In some embodiments, the kit consists of 4 variations of three peptides (e.g., peptides B, C, and D): 1) wild type phosphopeptide B, wild type non-phosphorylated peptide B, isotopically-enriched phosphopeptide B, and isotopically-enriched non-phosphorylated peptide B; 2) wild type phosphopeptide C, wild type non-phosphorylated peptide C, isotopically-enriched phosphopeptide C, and isotopically-enriched non-phosphorylated peptide C; and 3) wild type phosphopeptide D, wild type non-phosphorylated peptide D, isotopically-enriched phosphopeptide D, and isotopically-enriched non-phosphorylated peptide D.

The kit of the invention can comprise a chemical aliquot of a wild type or isotopically-enriched peptide that is about 0.001 to about 999 pg/mL, ng/mL, ug/mL, or mg/mL. In some embodiments, the kit of the invention can comprise a chemical aliquot of a wild type or isotopically-enriched peptide that is about 0.001, about 0.005, about 0.01, about 0.05, about 0.1, about 0.5, about 1, about 2.5, about 10, about 15, about 20, about 25, about 30, about 35, about 40, about 45, about 50, about 55, about 60, about 65, about 70, about 75, about 80, about 85, about 90, about 95, or about 100 pg/mL, ng/mL, ug/mL, or mg/mL. In some embodiments, the kit of the invention can comprise a chemical aliquot of a wild type or isotopically-enriched peptide that is about 100, about 125, about 150, about 175, about 200, about 225, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, or about 975 pg/mL, ng/mL, ug/mL, or mg/mL. In some embodiments, the chemical aliquot of wild type of isotopically-enriched peptides can be in femtomoles/μL (fmol/μL) or picomoles/μL (pmol/mL). In some embodiments, the invention can comprise a chemical aliquot of a wild type or isotopically-enriched peptide that is about 0.001-1000 fmol/μL or 1-1000 pmol/μL of plasma or a biological matrix.

The kit of the invention can comprise a sample of a phosphopeptide, wherein at least 0.01%, 0.1%, 0.5%, 1%, 2%, 3%, 4%, 5%, 6%, 7%, 8%, 9%, 10%, 11%, 12%, 13%, 14%, or 15% of the sample consists of molecules that have an amino acid residue that is isotopically-enriched.

The kit of the invention can be used to quantify the amount of phosphorylated peptides and corresponding phosphorylated proteins in buffy coat extracts from subjects with PAH by comparing test samples to control samples. In some embodiments, the kit can be used in an assay to compare the levels of phosphopeptides and corresponding phosphorylated proteins in subjects with PAH at specific time points compared to levels at different time points. In some embodiments, the peptide sequences are labeled with stable isotopes, such as $^{15}N$ or $^{13}C$, which are incorporated in the C-terminal arginine or lysine of a sequence.

The disclosed kit can include stable, isotopically-enriched peptides that have terminally- or internally-labeled peptides. In some embodiments, isotopically-enriched L-lysine (H2*N(*CH2)4*CH(*NH2)*COOH•2HCl) is incorporated into phosphorylated or non-phosphorylated peptides. In some embodiments, isotopically-enriched L-arginine (H2*N*C(=*NH)*NH(*CH2)3*CH(*NH2)*COOH•HCl) is incorporated into phosphorylated or non-phosphorylated peptides.

In some embodiments, the disclosed kit comprises at least one stable, isotopically-enriched internal standard. In some embodiments, the peptides of the kit can be used in an internal standard-triggered PRM-MS assay. In some embodiments, the kit comprises 1, 2, 3, 4, 5, 6, 7, 8, 9, or 10 stable, isotopically-enriched internal standards of TABLE 6 or TABLE 7. In some embodiments, the kit comprises, 1, 2, 3, 4, or 5 isotopically-enriched internal standards of TABLE 6 or TABLE 7. In some embodiments, the kit comprises 3 isotopically-enriched internal standards of TABLE 6 or TABLE 7.

In some embodiments, the kit is used to detect increased phosphorylation in 1, 2, 3, 4, 5, 6, 7, 8, 9, or 10 proteins. In some embodiments, the kit is used to detect increased phosphorylation in 1, 2, 3, 4, or 5 proteins. In some embodiments, the kit is used to detect increased phosphorylation in at least 3 proteins. In some embodiments, the kit is used to detect decreased phosphorylation in 1, 2, 3, 4, 5, 6, 7, 8, 9, or 10 proteins. In some embodiments, the kit is used to detect decreased phosphorylation in 1, 2, 3, 4, or 5 proteins. In some embodiments, the kit is used to detect decreased phosphorylation in at least 3 proteins.

In some embodiments, the kit is used to detect increased phosphorylation in 1, 2, 3, 4, 5, 6, 7, 8, 9, or 10 proteins and to detect decreased phosphorylation in 1, 2, 3, 4, 5, 6, 7, 8, 9, or 10 proteins. In some embodiments, the kit is used to detect increased phosphorylation in 1, 2, 3, 4, or 5 proteins and to detect decreased phosphorylation in 1, 2, 3, 4, or 5 proteins. In some embodiments, the kit is used to detect increased phosphorylation in 3 proteins and to detect decreased phosphorylation in 3 proteins.

Applications of the Invention

Proteins that are identified as having increased or decreased phosphorylation can be used as biomarkers for the diagnosis of PAH in a subject. In some embodiments, the phosphoprotein levels of a test sample can be compared to phosphoprotein levels of a non-PAH control sample to detect the presence of PAH. In some embodiments, the phosphoprotein levels of a test sample can be used to determine the progression of PAH by comparing the amount of phosphoproteins to amounts of phosphoproteins from a sample obtained at an earlier time. In some embodiments, phosphoprotein levels can be monitored and compared to phosphoprotein levels of samples obtained at earlier times to monitor the effects PAH therapy.

The disclosed invention can use a scoring system to determine the presence of PAH or to monitor the progression of PAH. In some embodiments, the difference in phosphoprotein levels of a test sample and a control sample is assigned a score. Phosphoprotein levels of more than one protein can be quantified in a test sample and to generate a total score. The score or total score of a sample can be compared to a score or total score of a control sample to diagnose or monitor the progression of PAH. In some embodiments, a score or total score of a sample that is higher than a score or total score of a control sample indicates the worsening of PAH. In some embodiments, a score or total score of a sample that is lower than a score or a total score of a control samples indicates the amelioration of PAH.

The disclosed invention can be used as a companion diagnostic for PAH treatment. The invention can also be used to detect or treat PAH due to left heart disease, including PH resulting from left ventricular systolic dysfunction, left ventricular diastolic dysfunction, valvular disease, congenital or acquired left heart inflow/outflow tract obstruction, and congenital cardiomyopathies.

The invention can detect or monitor PH treatment resulting from lung disease and/or hypoxia, including chronic obstructive pulmonary disease (COPD), interstitial lung disease, other pulmonary diseases with mixed restrictive and obstructive patterns, sleep-disordered breathing, alveolar hypoventilation disorders, chronic exposure to high altitude, and developmental lung diseases.

The invention can detect or monitor PH treatment resulting from chronic thromboembolic pulmonary hypertension (CTEPH). The invention can also detect or monitor PAH treatment resulting from unclear multifactorial mechanisms, including PAH resulting from hematologic disorders (e.g., chronic hemolytic anemia, myeloproliferative disorders, spienectomy), systemic disorders (e.g., sarcoidosis, pulmonary histiocytosis, lymphangioleiomyomatosis), metabolic disorders (e.g., glycogen storage disease, Gaucher disease, thyroid disorders), and other disorders, such as tumoral obstruction, fibrosing mediastinitis, chronic renal failure, and segmental PH.

The invention can be used to identify subjects with PAH, for example, PAH associated with dysregulated immune system activation. The invention can be used to identify subjects with heritable PAH associated with genetic mutations in the bone morphogenic type 2 receptor (BMPR2), activin-like kinase type 1 (ALK-1), endoglin (ENG), SMAD family member 9 (SMAD9), caveolin 1 (CAV1), or potassium two pore domain channel subfamily K member 3 (KCNK3). The invention can be used to identify subjects with PAH associated with connective tissue disease, HIV infection, portal hypertension, congenital heart diseases, schistosomiasis, pulmonary veno-occlusive disease, pulmonary capillary hemangiomatosis, or PPHN.

The invention can be used to detect changes in the levels of phosphoproteins. In some embodiments, the invention can detect changes in the levels of phosphoproteins and determine whether these changes correlate with clinically-important endpoints, such as mortality risk, hospitalization for PAH, and listing for lung transplant. Subsets of increased and/or decreased phosphoproteins in PMBCs can be used to identify subsets of subjects with poor prognoses who are less likely to respond to therapy.

EXAMPLES

I. Phosphoproteomic Analysis

Example 1

Obtaining iPAH and Control Tissue Samples

Samples from subjects with iPAH were obtained at the time of lung transplantation. Control samples were obtained from donor lungs that were free of pathology and not used for transplant.

TABLE 1 shows clinical characteristics of the iPAH and control subjects. The clinical data of TABLE 1 includes the diagnosis, age, and gender of each subject. The right heart catheterization (RHC) data includes a subject's right arterial (RA) pressure in mm Hg, mean pulmonary artery (PA) pressure in mm Hg, pulmonary capillary wedge pressure (PCWP) in mm Hg, and cardiac output (CO) in L/min. TABLE 1 also shows the medications that the subjects were receiving at the time the tissue samples were obtained, which include phosphodiesterase 5 (PDE-V) inhibitors, endothelin receptor (ET) antagonists, and prostanoids.

TABLE 1

| Clinical Data | | | | RHC Data | | | | Medications | | |
|---|---|---|---|---|---|---|---|---|---|---|
| Subject | Diagnosis | Age | Gender | RA mm Hg | Mean PA mm Hg | PCWP mm Hg | CO L/min | PDE-V Inhibitor | Endothelin Receptor Antagonist | Prostanoid |
| 1 | iPAH | 40 | F | 7 | 47 | 7 | 6.17 | | Ambrisentan | IV epoprostenol |
| 2 | iPAH | 41 | F | 30 | 55 | 7 | 3.86 | Sildenafil | Bosentan | IV epoprostenol |
| 3 | iPAH | 38 | F | NA | 50 | 8 | 2.87 | Sildenafil | Bosentan | IV treprostinil |
| 4 | iPAH | 25 | M | NA | 59 | 7 | 4.09 | Sildenafil | | IV epoprostenol/ SC treprostinil |
| 5 | iPAH | 40 | M | NA | 64 | 12 | 3.1 | Sildenafil | Ambrisentan | SC treprostinil |
| 6 | iPAH | 51 | M | NA | 50 | 8 | 4.6 | Sildenafil | | IV epoprostenol |
| 7 | APAH SSC | 54 | F | 10 | 55 | 10 | 5.47 | Sildenafil | Ambrisentan | IV epoprostenol |
| 8 | APAH SSC | 65 | F | 6 | 32 | 6 | 4.35 | Sildenafil | Bosentan | Inhaled treprostinil |
| 9 | APAH SSC | 55 | F | 11 | 51 | 11 | 5.9 | Sildenafil | Bosentan | IV epoprostenol |
| 10 | Control | 56 | F | | | | | | | |
| 11 | Control | 49 | F | | | | | | | |
| 12 | Control | 55 | F | | | | | | | |

TABLE 1-continued

| | Clinical Data | | | RHC Data | | | | Medications | | |
|---|---|---|---|---|---|---|---|---|---|---|
| Subject | Diagnosis | Age | Gender | RA mm Hg | Mean PA mm Hg | PCWP mm Hg | CO L/min | PDE-V Inhibitor | Endothelin Receptor Antagonist | Prostanoid |
| 13 | Control | 47 | M | | | | | | | |
| 14 | Control | 52 | M | | | | | | | |
| 15 | Control | 17 | M | | | | | | | |

Abbreviations:
iPAH = idiopathic PAH,
APAH SSC = PAH associated with systemic sclerosis or scleroderma;
RA = right atrial pressure,
PA = Pulmonary artery pressure;
PCWP = pulmonary capillary wedge pressure;
CO = cardiac output;
PDE-V = phosphodiesterase type V Example 2

Sample Preparation for Phosphoproteomic Analysis

Lung tissue obtained from subjects with iPAH was compared to lung tissue obtained from healthy subjects using phosphoproteomic analyses. Phosphoproteomic analyses were performed using frozen lung tissue from three iPAH female subjects, three male iPAH subjects, three healthy female subjects (female control), and three healthy male subjects (male controls).

The lung tissue samples of each sample group were homogenized in RIPA buffer (158 mM NaCl, 10 mM TRIS pH 7.2, 0.1% SDS, 1% Triton ×100, 1% deoxycholate, 1 mM EGTA, 40 mM beta-glycerophosphate, 30 mM sodium fluoride, 10 mM sodium pyrophosphate, 1 mM imidazole, 2 mM sodium orthovanadate, 1 Roche minitab protease inhibitor, 1 Roche minitab phosphostop tab/10 mL) using a Powergen™ homogenizer (VWR). The samples were spun by centrifuge at 10,000 rotations per minute (rpm), and the supernatant was sonicated and spun again.

The protein concentrations of the samples were determined using bicinchoninic acid (BCA) assays. The samples were stored at −80° C. until use. The proteins were precipitated with chloroform and methanol, resuspended in an 8 M urea/0.4M ammonium bicarbonate solution, and subjected to Lys C/trypsin digestion.

Whole lung homogenates for each group were pooled, enriched for phosphoproteins using strong cation exchange chromatography and repetitive $TiO_2$-based column chromatography (SCX/$TiO_2$), and subjected to LCMS/MS analyses.

Example 3

Phosphoproteomic Analyses of Tissue from Subjects with iPAH

A quantitative label-free phosphorproteomics strategy was used to identify peptides and to determine relative differences in phosphopeptides of the iPAH and control tissue samples.

Instrumentation: An LTQ Orbitrap ELITE™ (Thermo Scientific™) equipped with a Waters nanoAcquity™ ultra performance liquid chromatography (UPLC™) system, a Waters Symmetry® C18 180 μm×20 mm trap column, and a 1.7 μm, 75 μm×250 mm nanoAcquity™ UPLC™ column (35° C.) was used for peptide separation. Trapping was done using 99% of buffer A (0.1% formic acid in water) at a flow rate of 5 μL/min for 3 min. Peptide separation was performed with a linear gradient over 200 min using Buffer B (0.1% formic acid in acetonitrile) at a flow rate of 300 nL/min.

Data Analysis: Feature extraction, chromatographic/spectral alignment, data filtering, statistical analysis, and LFQ data were processed using Progenesis™ LC-MS software (Nonlinear Dynamics, LLC). The '.raw' data files were imported into the program, and a sample run was chosen as a reference. The reference was usually at or near the middle of all the runs in a sample set. All other runs were automatically aligned to the sample run to minimize retention time (RT) variability between runs. No adjustments were necessary in the m/z dimension due to the high mass accuracy of the spectrometer, which was typically <3 ppm. All runs were selected for detection with an automatic detection limit. The enriched and flow-through fractions were processed separately.

A normalization factor was then calculated for each run to account for differences in sample loads between injections. Multiple injections from each run were grouped together. The algorithm then calculated and tabulated raw and normalized abundances, max fold changes, and Anova values for each feature in the data set. The features were tagged in sets based on characteristics, such as MSMS>1 and p<0.05. The remaining MS/MS data were exported as a Mascot generic file (.mgf) for database searching. After the Mascot (Matrix Science) search, an .xml file of the results was created and imported into Progenesis™ LCMS software where search hits were assigned to corresponding features.

Database Searching: The '.mgf' files created by the Progenesis™ LC-MS software were searched and identified using a Mascot search algorithm for un-interpreted MS/MS spectra. Search parameters were as follows:
  The database searched: Swissprotein
  Taxonomy: human
  Confidence level: 95% within the Mascot search engine for protein hits based on randomness.
  Type of search: MS/MS ion search
  Enzyme: Trypsin/Lys C
  Variable modifications: carbamidomethyl (Cys), oxidation (Met), phospho (Ser, Thr, Tyr)
  Mass values: monoisotopic
  Protein mass: unrestricted
  Peptide mass tolerance: ±5 ppm
  Fragment mass tolerance: ±0.2 Da
  Charge: +7
  Max missed cleavages: 3
  Decoy: yes A confidence level of 95% meant that if 1500 peptides fell within the mass tolerance window about the precursor mass and the significance threshold was chosen to be 0.05 (95% confidence level), there would be a 1 in 20 chance of the protein identification being a false positive.

Using the Mascot database search algorithm, a protein was considered a positive hit when Mascot listed the pattern as significant and more than 2 unique peptides matched the same protein. A Mascot significance score match is based on a molecular weight search (MOWSE) score and relies on multiple matches to more than one peptide from the same protein. The Mascot search results were exported to an .xml file using a significance cutoff of p<0.05. Q values were also calculated.

The enriched phosphopeptide analysis generated 60,428 features. From these features, 6622 proteins were identified. Within the subset of identified proteins, 1480 phosphopeptides had q<0.05. The relative enrichment of phosphopeptides with q<0.05 in female iPAH vs. female controls, and male iPAH vs. male controls was determined.

TABLE 2 shows 10 phosphopeptides that had the highest phosphorylation ratios. Results show an increase in phosphorylation for IKZF3, HMHA1, BCAS3, RHG25, NUMA1, LEUK, MUC1, NU214, WDR24, AQR, 1A69, ASPP1, MK14, ZN404, OSB11, and HDGF.

IKZF3 phosphorylated at S378 had the highest phosphorylation ratio, and no phosphorylation was detected in the control samples. A high relative abundance of phosphorylated HMHA1 at S73 was also found. HMHA1 had a 6-fold increase in phosphorylation for male iPAH samples compared to male controls. BCAS3 phosphorylated at S709 exhibited a 119-fold increase for female iPAH samples and a 10-fold increase in male samples compared to their respective controls. The amount of phosphorylated RHG25 at T442 increased 18.95-fold in iPAH female samples and 2.75-fold for iPAH male samples.

NUMA1 phosphorylated at S2047 demonstrated a 15-fold increase in female iPAH samples. In male iPAH samples, NUMA1 phosphorylated at S2047 was not detected in the control, and provided an "infinite (∞)" increase in phosphorylation (i.e., male control denominator was zero). NUMA1 phosphorylated at S1969 increased by 15-fold in female iPAH samples compared to the corresponding control. NCOR1 phosphorylated at S999 showed a 7.4-fold increase in female iPAH samples compared to a 3.3-fold increase in male iPAH samples (data not shown).

The amount of phosphorylated ASPP1 at S710 increased 8.8-fold in iPAH females compared to the female control, and increased by 208.7-fold in male iPAH lung samples compared to the control. HDGF phosphorylated at S107 exhibited an 8.1-fold increase in female iPAH samples and a 37.1-fold increase in male iPAH samples compared to the respective controls.

TABLE 2

| SEQ ID NO. | Protein | Sequence | Variable modifications ([position] description) | Female iPAH/ Control | Male iPAH/ control) |
|---|---|---|---|---|---|
| 1 | IKZF3 | GLSPNNSGHDSTDTDSNHEER | [3] Phospho (S) | ∞ | ∞ |
| 2 | HMHA1 | HASAAGFPLSGAASWTLGR | [3] Phospho (S) | ∞ | 6.4908 |
| 3 | BCAS3 | HGSYDSLASDHSGQEDEEWLSQVEIVTHTGPHR | [6] Phospho (S) | 119.2601 | 10.7002 |
| 4 | RHG25 | RTQTLPNRK | [4] Phospho (T) | 18.9477 | 2.7541 |
| 5 | NUMA1 | RQSMAFSILNTPK | [3] Phospho (S) | 15.3163 | ∞ |
| 6 | LEUK | RPTLTTFFGR | [3] Phospho (T) | 11.9439 | 2.2581 |
| 7 | MUC1 | DTYHPMSEYPTYHTHGR | [11] Phospho (T) | 10.636 | 14.2286 |
| 8 | NU214 | TPSIQPSLLPHAAPFAK | [3] Phospho (S) | 10.3986 | 4.0896 |
| 9 | WDR24 | IIYCSPGLVPTANLNHSVGK | [4] Carbamidomethyl (C) [11] Phospho (T) | 10.2661 | 3.3501 |
| 10 | NUMA1 | RASMQPIQIAEGTGITTR | [3] Phospho (S) | 9.7252 | 12.1185 |
| 11 | AQR | DFSRYGRVNYVLARR | [10] Phospho (Y) | 9.5689 | 0.4385 |
| 12 | 1A69 | GGSYSQAASSDSAQGSDVSLTACK | [9] Phospho (S) [23] Carbamidomethyl (C) | 9.2518 | 24.0789 |
| 13 | ASPP1 | RSSITEPEGPGGPNIQK | [3] Phospho (S) | 8.8137 | 208.7079 |
| 14 | MK14 | HTDDEMTGYVATR | [7] Phospho (T) [9] Phospho (Y) | 8.7404 | 3.1787 |
| 15 | ZN404 | HSHLTEHQK | [5] Phospho (T) | 8.6749 | 3.6109 |

TABLE 2-continued

| SEQ ID NO. | Protein | Sequence | Variable modifications ([position] description) | Female iPAH/ Control | Male iPAH/ control) |
|---|---|---|---|---|---|
| 16 | OSB11 | RPSQNAISFFNVGHSK | [3] Phospho (S) | 8.3782 | 4.9584 |
| 17 | HDGF | SCVEEPEPEPEAAEGDGDK | [1] Phospho (S) [2] Carbamidomethyl (C) | 8.091 | 37.1543 |

Table nomenclature:
A square bracket, i.e., [3] means the amino acid position in the sequence that is phosphorylated or carbamidomethylated; the parentheses bracket means the amino acid at that position which is phosphorylated, i.e. (S). e.g., for SEQ ID NO. 1, the serine at position 3 in the sequence is phosphorylated. The IUPAC amino acid code system is used for amino acid abbreviations.

Western blots with custom-made phospho-specific (S378) antibody were analyzed to confirm that the amount of phosphorylated S378 IKZF3 was increased in iPAH lung extract relative to controls. A rabbit polyclonal IgG antibody was made against the N-terminus of IKZF3 and a phospho-specific site of IKZF3 at the C-terminus. The antibodies were subjected to affinity purification and negative adsorption. Phospho-specific and total antibodies against IKZF3 were used in Western blots to compare phospho-protein levels in iPAH, scleroderma-associated PAH (SSC-APAH), and control samples.

FIG. 1 Panel A shows that the signal for IKZF3 phosphorylated at S378 was higher in iPAH (n=5) samples compared to control samples (n=6). FIG. 1 Panel B shows that the signal for IKZF3 phosphorylated at S378 IKZF3 was higher in SSC-APAH samples (n=3) compared to control samples (n=3).

Immunohistochemistry experiments confirmed the presence of proteins in TABLE 2 and TABLE 3, and indicated immune and inflammatory cell involvement in the pathology of PAH. A custom pIKZF3 antibody was used for immunohistochemistry experiments. T cell markers and B cell markers were used to localize expression of pIKZF3 to specific cell types in iPAH, SSC-APAH, and control lung sections. Immunohistochemistry was also performed using an anti-HMHA1 antibody.

Figure 2:
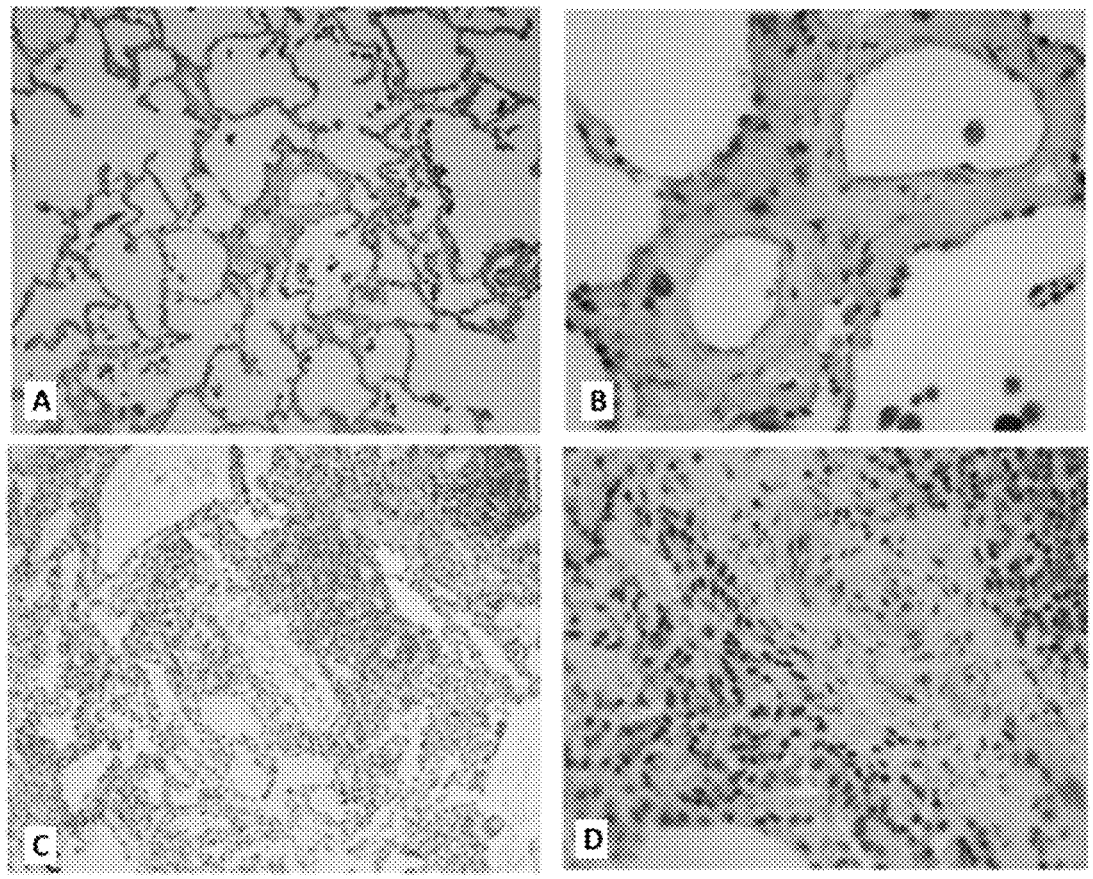
FIG. 2 shows immunohistochemistry results using a pIKZF3 antibody.

Immunohistochemistry experiments demonstrated that pIKZF3 in perivascular infiltrates in iPAH lung samples were predominantly T cells with some B cells present, neither of which were found in normal controls. Immunohistochemistry experiments also demonstrated that pIKZF3 in lymphocytes surrounding severely hypertrophied pulmonary arterioles. FIG. 2 shows that iPAH samples (FIG. 2 Panel C and FIG. 2 Panel D) had increased pIKZF3 in perivascular infiltrates compared to control samples (FIG. 2 Panel A and FIG. 2 Panel B). Cells staining positive for phosphorylated S378 IKZF3 densely surround a hypertrophied pulmonary arteriole. The perivascular infiltrates were found to contain of a mixed population of CD3$^+$, CD8$^+$ T cells, and CD20$^+$ B cells. CD45ra$^+$ T cells were also detected but to a lesser degree.

Figure 3:
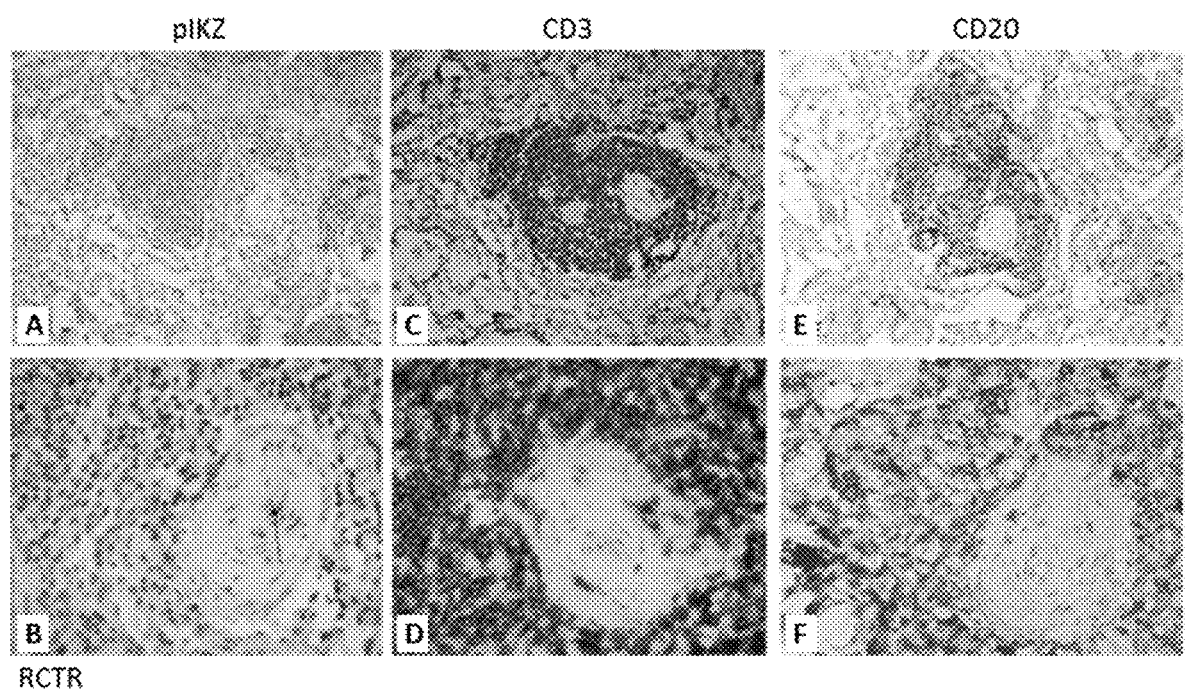
FIG. 3 shows immunohistochemistry of iPAH lung tissue and depicts inflammatory perivascular infiltrates.

FIG. 3 shows the immunohistochemistry of iPAH lung tissue and shows inflammatory perivascular infiltrates. CD3: antibody against a T cell marker; CD20: antibody against a B cell marker; pIKZF3: antibody against S378 pIKZF3. pIKZF3 was predominantly present in perivascular cells, but were also seen in endothelial-like cells of the diseased pulmonary arteriole. The perivascular cells were predominantly T cells with some B cells present which were not found in normal controls.

FIG. 3 Panel A shows pIKZF3 with a 10× objective. FIG. 3 Panel B shows pIKZF3 with a 40× objective. The arrow points to a small lumen of a pulmonary arteriole with staining of the endothelium. FIG. 3 Panel C shows CD3 T cell markers with a 10× objective. FIG. 3 Panel D shows CD3 T cell markers with a 40× objective. The T cells were primarily found to be perivascular, and more T cells were found than B cells. FIG. 3 Panel E shows the CD20 B cell marker with a 10× objective. FIG. 3 Panel F shows the CD20 B cell marker with a 40× objective.

Figure 4:
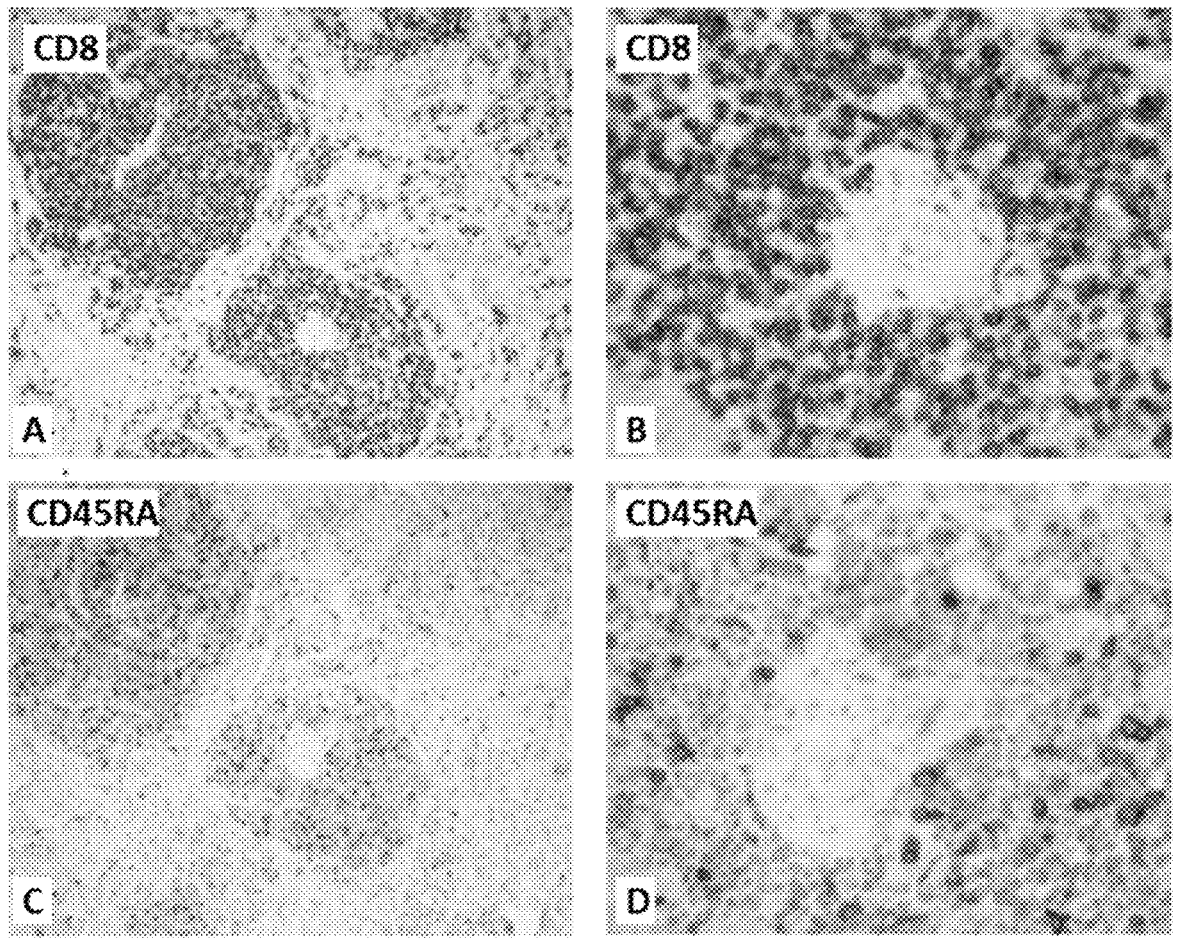
FIG. 4 shows the perivascular infiltrates of iPAH lung sections.

FIG. 4 shows that the perivascular infiltrates seen in iPAH lung sections were highly positive for CD8 (FIG. 4 Panel A: 10× objective; FIG. 4 Panel B: 40× objective). Scattered cells in the perivascular infiltrates stained positive for CD45RA. CD45RA is a protein tyrosine phosphatase and is used as a marker for cytolytic T lymphocytes.

Figure 5:
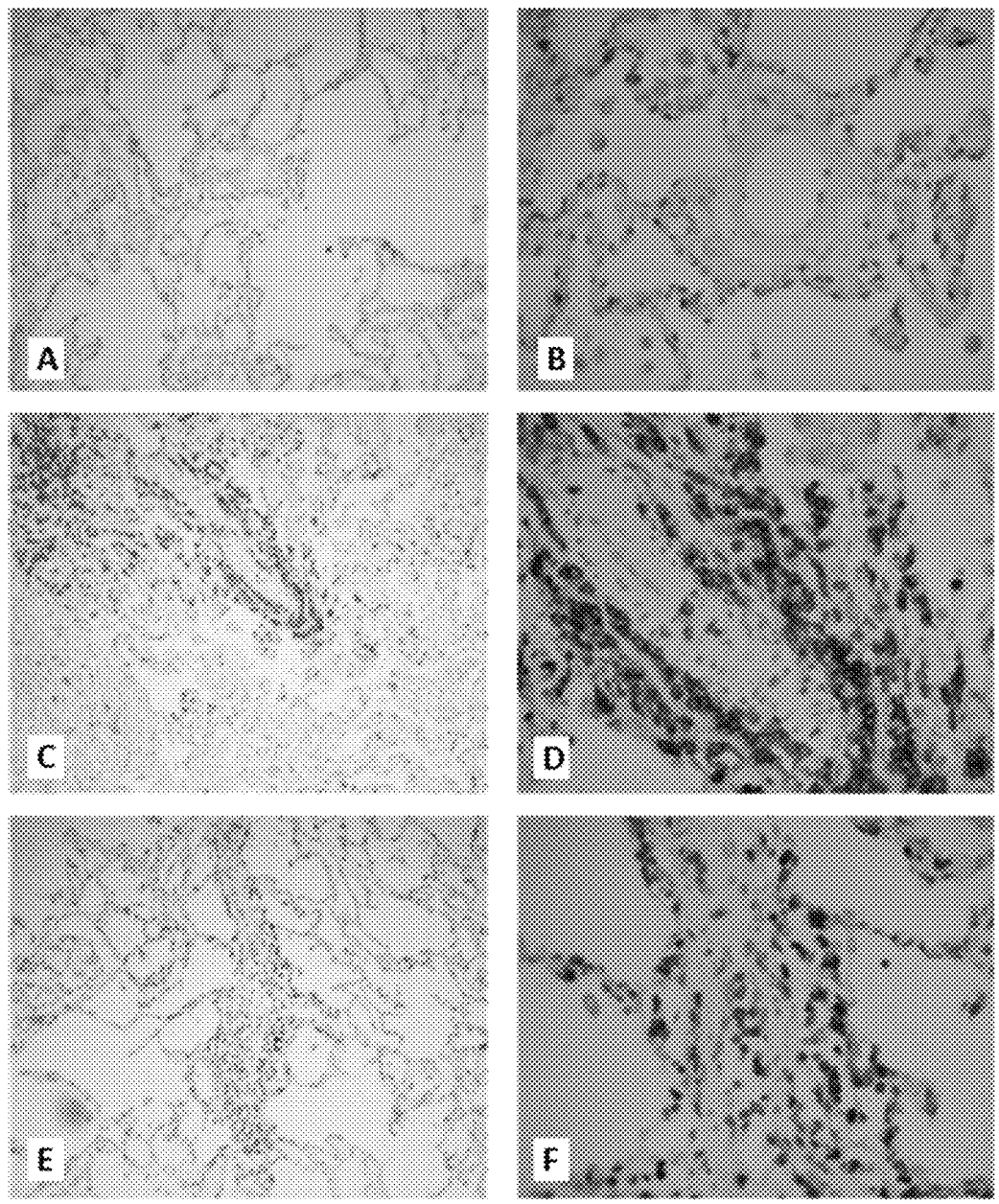
FIG. 5 shows HMHA1 in perivascular infiltrates in SSC-APAH lung samples.

HMHA1 was also localized to perivascular infiltrates surrounding remodeled pulmonary arterioles. Cells surrounding a pulmonary arteriole were highly positive for HMHA1 in the SSC-APAH sample. FIG. 5 Panel A and Panel B show HMHA1 in normal controls. FIG. 5 Panel C and 5 Panel D show perivascular infiltrates in SSC-APAH lung samples (FIG. 5 Panel C: 10× objective; FIG. 5 Panel D: 40× objective). FIG. 5 Panel E and 5 Panel F show HMHA1 in perivascular infiltrates in iPAH lung samples (FIG. 5 Panel E: 10× objective; FIG. 5 Panel F: 40× objective).

TABLE 3 shows 10 phosphopeptides that had the lowest phosphorylation ratios. Phosphorylated proteins that exhibited low relative abundance compared to control samples in iPAH female and male samples included phosphorylated forms of PTPRB, SNG2L, HTSF1, PSIP1, ANXA2, S10A9, RLA2, TM100, SRSF2, PLD1, BI2L2, TENS1, MAP1B, and CTNA1.

Phosphorylation of HDAC2 at S422 was decreased in female and male iPAH lung samples compared to controls. Phosphorylation of PTPRB was completely absent at S119.

TABLE 3

| SEQ ID NO. | Protein | Sequence | Variable modifications ([position] description) | Female PAH/ Control | Male PAH/ Control |
|---|---|---|---|---|---|
| 18 | PTPRB | FGVSKEK | [4] Phospho (S) | 0.00 | 0.00 |
| 19 | SNG2L | ALCLVFALIVFSCIYGEGYSNTHKSK | [3] Carbamidomethyl (C)<br>[13] Carbamidomethyl (C)<br>[19] Phospho (Y)<br>[20] Phospho (S)<br>[22] Phospho (T)<br>[25] Phospho (S) | 0.01 | 0.27 |
| 20 | HTSF1 | VLDEEGSEREFDEDSDEKEEEEDTYEK | [15] Phospho (S) | 0.02 | 0.28 |
| 21 | PSIP1 | TGVTSTSDSEEEGDDQEGEK | [9] Phospho (S) | 0.02 | 0.04 |
| 22 | ANXA2 | IMVSRSEVDMLKIR | [4] Phospho (S)<br>[10] Oxidation (M) | 0.02 | 0.08 |
| 23 | S10A9 | MHEGDEGPGHHHKPGLGEGTP | [20] Phospho (T) | 0.07 | 0.80 |
| 24 | RLA2 | KEESEESDDDMGFGLFD | [7] Phospho (S) | 0.08 | 0.04 |
| 25 | TM100 | RRESQTALVANQR | [4] Phospho (S) | 0.12 | 0.43 |
| 26 | SRSF2 | SRSPPPVSK | [3] Phospho (S) | 0.13 | 0.28 |
| 27 | PLD1 | MSLKNEPRVNTSALQK | [11] Phospho (T)<br>[12] Phospho (S) | 0.18 | 0.82 |
| 28 | BI2L2 | LMSSEQYPPQELFPR | [3] Phospho (S) | 0.21 | 1.36 |
| 29 | TENS1 | AASDGQYENQSPEATSPRSPGVR | [3] Phospho (S)<br>[16] Phospho (S)<br>[19] Phospho (S) | 0.21 | 0.90 |
| 30 | MAP1B | RESVASGDDRAEEDMDEAIEK | [3] Phospho (S) | 0.22 | 0.19 |
| 31 | CTNA1 | SRTSVQTEDDQLIAGQSAR | [4] Phospho (S) | 0.24 | 0.29 |

Table nomenclature:
A square bracket, i.e., [3] means the amino acid position in the sequence that is modified; the parentheses bracket means the amino acid at that position which is modified, i.e. (S). e.g., for SEQ ID NO. 18, the serine at position 4 in the sequence is phosphorylated.
Abbreviations for modifications:
Phospho = phosphorylation;
Carbamidomethyl = carbamidomethylation.
S = serine,
T = Threonine,
Y = tyrosine.
The IUPAC amino acid code system is used for amino acid abbreviations.

II. Using Biomarkers to Detect and Diagnose PAH

Example 4

Preparing Samples for Use in Biomarker Assays

PBMCs or buffy coats are lysed in RIPA buffer (158 mM NaCl, 10 mM TRIS pH 7.2, 0.1% SDS, 1% Triton ×100, 1% deoxycholate, 1 mM EGTA, 40 mM beta-glycerophosphate, 30 mM sodium fluoride, 10 mM sodium pyrophosphate, 1 mM imidazole, 2 mM sodium orthovanadate, 1 Roche minitab protease inhibitor, 1 Roche minitab phosphostop tab/10 mL) and spun by centrifuge at 14,000 rpm for 10 minutes. After centrifugation, the supernatants are collected and proteins are precipitated using a methanol-chloroform mixture.

The resulting protein pellets are resuspended in 0.1 M tetraethyl ammonium bromide (TEAB)/0.1% RapiGest™ buffer, reduced with tris(2-carboxyethyl)phosphine (TCEP) for 60 minutes at 55° C., and then alkylated with iodoacetamide for 30 min at room temperature in the dark. The denatured proteins are digested with trypsin by incubating the samples overnight at 37° C. The peptide concentration of the tryptic digest is determined by amino acid analysis using a Hitachi L-8900 Amino Acid Analyzer™. The tryptic digests are enriched for phosphopeptides using a TiO$_2$ enrichment kit (ThermoFisher Scientific™) and desalted using Sep-Pak cartridges.

The enriched phosphopeptides are spiked with stable isotope-labeled phosphopeptide internal standards, and the mixture is subjected to PRM-MS analysis. Buffy coat samples can also be labeled with internal standards and unlabeled phosphopeptides to determine extraction efficiencies. Quality control samples at low, medium, and high concentration are included in the analyses. Precision, accuracy, linear range, lowest limit of detection (LLOD), and lowest limit of quantification (LLOQ) levels are determined for the entire phosphopeptide set.

Acceptance criteria: Linearity is 4 to 5 orders of magnitude and has coefficients of variability of ≤10%. LLOQ is defined as the lowest concentration where the coefficient of variation (CV) of triplicate injections is less than 20% with an average accuracy within 80-120%. Above the LLOQ, the accuracy (measured-nominal)/measured concentration is ±15%. Precision (SD of replicates)/mean of replicates is ≤15%. Sensitivity is on the order of femtomoles/ml and is similar to some enzyme-linked immunosorbent (ELISA) assays.

Mass spectrometric data acquisition: The samples are analyzed using PRM on an Orbitrap-Fusion™ Tribrid™ MS interfaced at the front end with a Waters® nanoACQUITY UPLC® System. First, a spectral library is generated by performing data-dependent acquisition (DDA) in the Orbitrap-Fusion™. For DDA, a full-scan MS spectrum (m/z range 400-1600) is acquired in the Orbitrap region with a resolution of 120,000, automatic gain control (AGC) target of $4\times10^5$, and maximum injection time of 50 ms. The precursor ions for MS/MS are selected based on and starting from the most intense ion in the full-scan MS spectra. The precursor ions for MS/MS are in the quadrupole region with an isolation window of 1.6 m/z, and are fragmented by higher-collisional energy dissociation (HCD) in the ion trap region with normalized collision energies set to 28. The fragmentation spectra are acquired in the Orbitrap region with a resolution of 60,000, AGC target of $1\times10^5$, and maximum injection time of 120 ms. Selection and fragmentation of ions contain a dynamic exclusion setting of 15 s to minimize repeat sequencing of peptides.

For PRM-MS, the Orbitrap-Fusion™ MS is operated in targeted-$MS^2$ data acquisition mode. Information, such as the precursor m/z, charge state, and elution time needed to build the inclusion list for the analysis of the target light and heavy peptides by PRM are obtained from the acquired DDA data. The data acquisition parameters for PRM are similar to parameters for the MS/MS scans in DDA mode. The cycle time of the MS/MS scans are kept to 3 s or less to obtain at least 10 data points across chromatographic peaks, assuming the average width of a chromatograph is ~30 s.

To increase the number of phosphopeptides for the assay list, a scheduled PRM method can be implemented. In the scheduled PRM method, target peptides are only targeted over a preselected LC retention time, as determined in the first DDA experiment. The spectral library is used in Skyline analysis software to assign and quantify target peptides. Scheduled monitoring also ensures the highest plexing capabilities for the various peptides to be quantified. Scheduling means that test samples are run to determine the precise retention time associated with each of the target peptides.

Data analysis: The MS raw data from DDA analysis are processed using Proteome Discoverer™ v2.0 (Thermo Scientific) software. The files are searched against the human SwissProt database using Sequest HT and Mascot search algorithms. Peptide spectrum matches (PSMs) are verified based on q-values set to a 1% false discovery rate (FDR) using Percolator (Matrix Science). The list of proteins and peptides identified serve as the spectral library for the PRM data analysis in Skyline software. Quantification of a targeted peptide is based on the top five ranked product ions of each precursor ion selected.

The processed Skyline data is manually verified, and product ions with interferences are removed and replaced with the next highest-ranking product ions. The ratios of integrated peak areas of fragment ions of light to heavy peptides across the samples are used for relative quantification of the samples. Phosphorylation at a site of interest is normalized to the average abundance of several non-phosphorylated sites of the protein to create a relative abundance value for the degree of phosphorylation.

Example 5

Phosphatase Inhibitor Treatment of Buffy Coat Extracts

A stability study is performed to determine the effects of adding an inhibitor cocktail directly to blood samples, adding an inhibitor cocktail after isolation of the buffy coat, or washing the buffy coat cells with buffer containing an inhibitor cocktail after isolation but prior to extraction. Stability of the buffy coat extracts is determined using a PRM-MS assay and Western blot analyses for selected phosphoproteins using research grade phospho-specific antibodies. Phospho-specific antibodies for stability studies include antibodies for pIKZF3, pNUMA1, and pHDAC2.

The samples are collected in BD Vacutainer® CPT™ Cell Preparation Tubes with sodium citrate and ficoll following BD's published collection procedure (REF 362761). The collection procedure spins by centrifuge, separates, washes, and concentrates the PBMCs for further use. The collection procedure is modified by adding a phosphatase inhibitor cocktail or washing the cells with a buffer containing the inhibitor cocktail to preserve the stability of the phosphoproteins.

A phosphatase inhibitor cocktail is added to blood samples at the time of blood collection or to the buffy coat after isolation from PBMCs. A non-lysing non-denaturing inhibitor cocktail is added to blood samples. For buffy coat samples, the samples are resuspended in a lysing buffer and snap frozen in liquid nitrogen for storage prior to assaying the samples. Both non-phosphatase-inhibited and phosphatase-inhibited samples are tested to determine whether phosphatase inhibition is required and, if so, required at what stage of the collection process. Samples are considered acceptable when less than 25% degradation in signal.

Extraction of proteins: The cytoplasmic proteins, including the phosphoproteins, are extracted from the PBMCs following the Thermo Fisher™ (Pierce) procedure 89900 and using RIPA buffer. This procedure is compatible with or without the phosphate inhibitor cocktail. Protein extraction from the PBMCs is tested by quantifying total protein content, total phosphoprotein content, and identifying of each specific phosphoprotein resulting from the proteomic analysis described above.

Example 6

Baseline Screening of Control Samples and PAH Samples

Buffy coat cells and PBMCs are collected from subjects with PAH, SSC subjects without PAH, and healthy subjects. A Health Insurance Portability and Accountability Act (HIPAA) compliant database allows for analysis of clinical parameters. The database has restricted access, and subject identifiers are removed prior to release of clinical data matched to samples. The clinical courses of study subjects are followed over time, and changes in candidate biomarkers over time are correlated with clinical outcome.

Clinical parameters include age, gender, PH classification, genetic markers (i.e., presence of BMPR2 mutations, ALK, or endoglin mutations), medications, functional class, six-minute walk distance, cardiopulmonary hemodynamics, and clinical course (i.e., hospitalization, listing for lung transplant, mortality).

The study is performed using a test data set and a verification data set. The test set enrolls subjects with PAH (n=30 iPAH, n=30 SSC-APAH), subjects with SSC without PAH (n=20), and normal controls (n=20). The verification set uses assays (described above) that show significant differences between PAH subjects and normal controls to screen a similar cross section of subjects with PAH (n=30 iPAH, n=30 SSC APAH), subjects with SSC but without PAH (n=20), and normal controls (n=20).

The results of PRM-MS assays for designated phosphoproteins are correlated with parameters in the clinical database, listed above. Inclusion criteria include: age >18 yrs, diagnosis of PAH, SSC without PAH, or normal controls. Subjects acting as normal controls have no history of systemic illness such as hypertension, DM, thyroid disease, bleeding abnormality, active infection, asthma, cancer, renal failure, smoking, or drug abuse. Exclusion criteria include: age <18 yrs, co-morbid conditions such as current cancer, or treatment with immunosuppressants including steroids.

Analyses: Analyses of biomarkers for the diagnosis of PAH (present/absent) and analyses of biomarkers for prognosis of PAH (good/bad) are conducted. Analyses of biomarkers for prognosis of PAH attempt to identify the set of phosphoproteins that predict worsening PAH. Worsening PAH includes an increase in mortality, increase in hospitalization for PAH, decrease in six-minute walk distance (6MWD), worsening functional class, need for lung transplantation, or need for addition of a prostanoid.

The Wilcoxon rank sum test is used to determine the association between individual phosphoprotein biomarkers and the presence of PAH or the worsening of PAH. Phosphoprotein levels are analyzed using logistic regression. Regression coefficients are combined to form "classifier scores." Diagnostic tests are determined to be positive or negative when the linear combination is either ≥ or < than a cut-off threshold. For a given cut-off threshold, ROC curves are generated by plotting sensitivity vs 1-specificity. All biomarker subsets are examined to evaluate the predictive value of each subset.

After identifying candidate logistic regression models, the models are "tuned" using cross validation. The minmax concave penalty method (MCP) is also used for variable selection, which has larger predictive AUCs for ROC curves. Upon identifying the best model, the model is applied to a verification set. A power calculation for logistic regression is performed using XLSTAT™ (Pearson) or a similar program. Parameters for a sample size of 30 includes: alpha set at 0.05, baseline probability of 0.1, alternative probability of 0.7: beta=0.057, and power=0.943. If alternative probability is set at 0.6, then the power decreases to 0.85.

Example 7

Stable, Isotopically-Enriched Peptide Sequences

Stable, isotopically-enriched variants of the peptides in TABLE 2 and TABLE 3 are prepared and used as internal standards in PRM-MS assays to detect or monitor the progression of PAH. In some embodiments, stable, isotopically-enriched arginine (R) or lysine (K) is introduced at the C-terminus of each peptide of TABLE 2 and TABLE 3 and the corresponding non-phosphorylated peptides. In some embodiments, stable, isotopically-enriched arginine (R) or lysine (K) is embedded in the sequence of each peptide of TABLE 2 and TABLE 3 and the corresponding non-phosphorylated peptides.

TABLE 4 shows an example of isotopically-labeled L-arginine used to synthesize stable, isotopically-enriched peptides. TABLE 5 shows an example of isotopically-labeled L-lysine used to synthesize stable, isotopically-enriched peptides.

TABLE 4

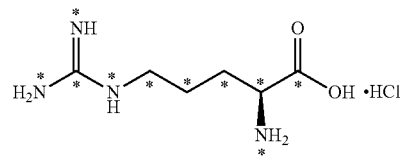 [SMILES: N=C(N)NCCC[C@H](N)C(=O)O ; Cl]

L-Arginine: HCl (13C6, 99%; 15N4, 99%)

| | |
|---|---|
| Chemical formula | H2*N*C(=*NH)*NH(*CH2)3*CH(*NH2)*COOH•HCl |
| Unlabeled CAS# | 1119-34-2 |
| Labeled CAS# | 202468-25-5 |
| Molecular weight | 220.59 |
| Chemical purity | 98% |

TABLE 5

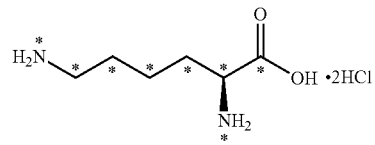

L-Lysine: 2HCl (13C6, 99%; 15N2, 99%)

| | |
|---|---|
| Chemical formula | H2*N(*CH2)4*CH(*NH2)*COOH•2HCl |
| Unlabeled CAS# | 657-26-1 |
| Labeled CAS# | N/A |
| Molecular weight | 227.05 |
| Chemical purity | 98% |

TABLE 6 shows stable, isotopically-labeled phosphorylated and non-phosphorylated peptides of the 17 phosphopeptides that had the highest phosphorylation ratios (TABLE 2), and can be used as standards in PRM-MS assays. The phosphorylated and non-phosphorylated peptide sequences are shown with variable modifications. The variable phosphorylated amino acids are shown in parentheses (e.g., (S) or (T)). Stable, isotopically-enriched amino acids are shown in curly brackets (e.g., {K}).

TABLE 7 shows stable, isotopically-labeled phosphorylated and non-phosphorylated peptides of 14 phosphopeptides that had the lowest phosphorylation ratios (TABLE 3), and can be used as standards in PRM-MS assays. The phosphorylated and non-phosphorylated peptide sequences are shown with variable modifications. The variable phosphorylated amino acids are shown in parentheses (e.g., (S)). Stable, isotopically-enriched amino acids are shown in curly brackets (e.g., {K}).

TABLE 6

| Protein | SEQ ID NO. | Phosphorylated peptide for PRM assay | SEQ ID NO. | Nonphosphorylated peptide for PRM assay |
|---|---|---|---|---|
| IKZF3_HUMAN | 32 | GL(S)PNNSGHDSTDTDSNHEE{R} | 33 | GLSPNNSGHDSTDTDSNHEE{R} |
| HMHA1_HUMAN | 34 | HA(S)AAGFPLSGAASWTLG{R} | 35 | HASAAGFPLSGAASWTLG{R} |
| BCAS3_HUMAN | 36 | HGSYD(S)LASDHSGQEDEEWLSQVEIVTHTGPH{R} | 37 | HGSYDSLASDHSGQEDEEWLSQVEIVTHTGPH{R} |
| RHG25_HUMAN | 38 | RTQ(T)LPNR{K} | 39 | RTQTLPNR{K} |
| NUMA1_HUMAN | 40 | RQ(S)MAFSILNTP{K} | 41 | RQSMAFSILNTP{K} |
| LEUK_HUMAN | 42 | RPTLTTFFG{R} | 43 | RPTLTTFFG{R} |
| MUC1_HUMAN | 44 | DTYHPMSEYP(T)YHTHG{R} | 45 | DTYHPMSEYPTYHTHG{R} |
| NU214_HUMAN | 46 | TP(S)IQPSLLPHAAPFA{K} | 47 | TPSIQPSLLPHAAPFA{K} |
| WDR24_HUMAN | 48 | IIYCSPGLVP(T)ANLNHSVG{K} | 49 | IIYCSPGLVPTANLNHSVG{K} |
| NUMA1_HUMAN | 50 | RA(S)MQPIQIAEGTGITT{R} | 51 | RASMQPIQIAEGTGITT{R} |
| AQR_HUMAN | 52 | DFSRYGRVN(Y)VLA{R} | 53 | DFSRYGRVNYVLA{R} |
| 1A69_HUMAN | 54 | GGSYSQAA(S)SDSAQGSDVSLTAC{K} | 55 | GGSYSQAASSDSAQGSDVSLTAC{K} |
| ASPP1_HUMAN | 56 | RS(S)ITEPEGPGGPNIQ{K} | 57 | RSSITEPEGPGGPNIQ{K} |
| MK14_HUMAN | 58 | HTDDEM(T)G(Y)VAT{R} | 59 | HTDDEMTGYVAT{R} |
| ZN404_HUMAN | 60 | HSHL(T)EHQ{K} | 61 | HSHLTEHQ{K} |
| OSB11_HUMAN | 62 | RP(S)QNAISFFNVGHS{K} | 63 | RPSQNAISFFNVGHS{K} |
| HDGF_HUMAN | 64 | (S)CVEEPEPEPEAAEGDGD{K} | 65 | SCVEEPEPEPEAAEGDGD{K} |

Parentheses (e.g., (S) or (T)) indicate phosphorylation of the amino acid
Curly brackets (e.g., {K}) indicate a stable, isotopically labeled amino acid

TABLE 7

| Protein | SEQ ID NO. | Phosphorylated peptide for PRM assay | SEQ ID NO. | Nonphosphorylated peptide for PRM assay |
|---|---|---|---|---|
| PTPRB_HUMAN | 66 | FGV(S)KE{K} | 67 | FGVSKE{K} |
|  | 68 | PARFGV(S)KE{K} | 69 | PARFGVSKE{K} |
| SNG2L_HUMAN | 70 | ALCLVFALIVFSCIYGEG(Y)(S)N(T)HK(S){K} | 71 | ALCLVFALIVFSCIYGEGYSNTHKS{K} |
|  | 72 | IYGEG(Y)(S)N(T)HK(S){K} | 73 | IYGEGYSNTHKS{K} |
| HTSF1_HUMAN | 74 | VLDEEGSEREFDED(S)DEKEEEEDTYE{K} | 75 | VLDEEGSEREFDEDSDEKEEEEDTYE{K} |
| PSIP1_HUMAN | 76 | TGVTSTSD(S)EEEGDDQEGE{K} | 77 | TGVTSTSDSEEEGDDQEGE{K} |
| ANXA2_HUMAN | 78 | IMV(S)RSEVDMLKI{R} | 79 | IMVSRSEVDMLKI{R} |
|  | 80 | V(S)RSEVDMLKI{R} | 81 | VSRSEVDMLKI{R} |
| S10A9_HUMAN | 82 | MHEGDEGPGHHH{K}PGLGEG(T)P | 83 | MHEGDEGPGHHH{K}PGLGEGTP |
|  | 84 | HEGDEGPGHHH{K}PGLGEG(T)P | 85 | HEGDEGPGHHH{K}PGLGEGTP |
| RLA2_HUMAN | 86 | {K}EESEE(S)DDDMGFGLFD | 87 | {K}EESEESDDDMGFGLFD |
| TM100_HUMAN | 88 | RRE(S)QTALVANQ{R} | 89 | RRESQTALVANQ{R} |
| SRSF2_HUMAN | 90 | SR(S)PPPVS{K} | 91 | SRSPPPVS{K} |
| PLD1_HUMAN | 92 | MSLKNEPRVN(T)(S)ALQ{K} | 93 | MSLKNEPRVNTSALQ{K} |
|  | 94 | SLKNEPRVN(T)(S)ALQ{K} | 95 | SLKNEPRVNTSALQ{K} |
| BI2L2_HUMAN | 96 | LM(S)SEQYPPQELFP{R} | 97 | LMSSEQYPPQELFP{R} |

TABLE 7-continued

| Protein | SEQ ID NO. | Phosphorylated peptide for PRM assay | SEQ ID NO. | Nonphosphorylated peptide for PRM assay |
|---|---|---|---|---|
| TENS1_HUMAN | 98 | AA(S)DGQYENQSPEAT(S)PR(S)PGV{R} | 99 | AASDGQYENQSPEATSPRSPGV{R} |
| MAP1B_HUMAN | 100 | RE(S)VASGDDRAEEDMDEAIE{K} | 101 | RESVASGDDRAEEDMDEAIE{K} |
| CTNA1_HUMAN | 102 | SRT(S)VQIEDDQLIAGQSA{R} | 103 | SRT SVQTEDDQLIAGQSA{R} |

Parentheses (e.g., (S) or (T)) indicate phosphorylation of the amino acid
Curly brackets (e.g., {K}) indicate a stable, isotopically labeled amino acid Embodiments The following non-limiting embodiments provide illustrative examples of the invention, but do not limit the scope of the invention.

Embodiment 1. A method comprising: a) adding to a sample of a protein extracted from a buffy coat an amount of a quantification standard to provide a test sample; and b) assaying the test sample to quantify in the test sample a wild type phosphopeptide of the protein extracted from the buffy coat, wherein the quantifying is based on the amount of the quantification standard, wherein the quantification standard is a form of the phosphopeptide that is isotopically-enriched to a non-natural abundance of an isotope.

Embodiment 2. The method of embodiment 1, further comprising: a) obtaining a tissue sample from a human subject, wherein the tissue sample contains the buffy coat; and b) isolating the protein from the tissue sample to provide the sample of the protein.

Embodiment 3. The method of any one of embodiments 1-2, further comprising digesting the sample of protein prior to adding the amount of the quantification standard.

Embodiment 4. The method of any one of embodiments 2-3, wherein the human subject has pulmonary hypertension.

Embodiment 5. The method of any one of embodiments 2-4, wherein the human subject has pulmonary arterial hypertension.

Embodiment 6. The method of any one of embodiments 4-5, wherein the pulmonary hypertension is idiopathic pulmonary hypertension.

Embodiment 7. The method of any one of embodiments 4-5, wherein the pulmonary hypertension is pulmonary hypertension associated with systemic sclerosis.

Embodiment 8. The method of any one of embodiments 1-7, wherein the quantification standard is an isotopically-enriched peptide of TABLE 2 or TABLE 3.

Embodiment 9. The method of any one of embodiments 1-7, wherein the quantification standard is an isotopically-enriched peptide of TABLE 6 or TABLE 7.

Embodiment 10. The method of any one of embodiments 1-9, wherein the quantifying is performed by mass spectrometry.

Embodiment 11. The method of any one of embodiments 1-10, wherein the quantifying is performed by parallel reaction monitoring mass spectrometry.

Embodiment 12. The method of any one of embodiments 1-9, wherein the quantifying is performed by contacting the test sample with a phospho-specific antibody.

Embodiment 13. The method of any one of embodiments 1-12, wherein the quantifying comprises detecting a ratio of the wild type phosphopeptide amount to an amount of a non-phosphorylated form of the wild type peptide.

Embodiment 14. The method of embodiment 13, wherein the ratio of the amount of the wild type phosphopeptide to the amount of the non-phosphorylated form of the wild type peptide is greater than a corresponding ratio obtained from a control sample obtained from a test subject that has pulmonary arterial hypertension.

Embodiment 15. The method of embodiment 13, wherein the ratio of the amount of the wild type phosphopeptide to the amount of the non-phosphorylated form of the wild type peptide is less than a corresponding ratio obtained from a control sample obtained from a test subject that has pulmonary arterial hypertension.

Embodiment 16. The method of embodiment 13, wherein the ratio of the amount of the wild type phosphopeptide to the amount of the non-phosphorylated form of the wild type peptide is greater than a corresponding ratio obtained from a test subject that does not have pulmonary arterial hypertension.

Embodiment 17. The method of embodiment 13, wherein the ratio of the amount of the wild type phosphopeptide to the amount of the non-phosphorylated form of the wild type peptide is less than a corresponding ratio obtained from a test subject that does not have pulmonary arterial hypertension.

Embodiment 18. A chemical aliquot comprising a sample of a phosphopeptide, wherein at least 1% of the sample of the phosphopeptide consists of molecules that have an amino acid residue that has at least two $^{13}$C nuclei, wherein the sample contains at least 1 pg of the phosphopeptide, wherein the phosphopeptide has at least 90% sequence identity to any compound of TABLE 2 or TABLE 3.

Embodiment 19. The chemical aliquot of embodiment 18, wherein at least 10% of the sample of the phosphopeptide consists of molecules that have the amino acid residue that has at least two $^{13}$C nuclei.

Embodiment 20. The chemical aliquot of any one of embodiments 18-19, wherein at least 50% of the sample of the phosphopeptide consists of molecules that have the amino acid residue that has at least two $^{13}$C nuclei.

Embodiment 21. The chemical aliquot of any one of embodiments 18-20, wherein the amino acid residue that has at least two $^{13}$C nuclei has at least three $^{13}$C nuclei.

Embodiment 22. The chemical aliquot of any one of embodiments 18-20, wherein the amino acid residue that has at least two $^{13}$C nuclei has six $^{13}$C nuclei.

Embodiment 23. The chemical aliquot of any one of embodiments 18-22, wherein the amino acid residue that has at least two $^{13}$C nuclei has at least two $^{15}$N nuclei.

Embodiment 24. The chemical aliquot of any one of embodiments 18-23, wherein the amino acid that has at least two $^{13}$C nuclei residue is lysine.

Embodiment 25. The chemical aliquot of any one of embodiments 18-23, wherein the amino acid residue that has at least two $^{13}$C nuclei is arginine.

Embodiment 26. A kit comprising: a) a chemical aliquot comprising a sample of a phosphopeptide, wherein at least 1% of the sample of the phosphopeptide consists of molecules that have an amino acid residue that has at least two $^{13}C$ nuclei, wherein the sample contains at least 1 pg of the phosphopeptide, wherein the phosphopeptide has at least 90% sequence identity to any compound of any of TABLE 2 or TABLE 3; and b) an additional aliquot comprising a sample of the phosphopeptide that has nuclei in a natural abundance of isotopes.

Embodiment 27. A method comprising: a) obtaining a test sample of tissue from a subject; b) assaying the test sample to quantify in the test sample a phosphorylation level of a peptide; c) comparing the phosphorylation level of the peptide to a phosphorylation level of a corresponding peptide in a control sample; d) based on the comparing the phosphorylation level of the peptide to the phosphorylation level of the corresponding peptide in the control sample, determining whether the subject suffers from a pulmonary condition; and e) based on the determining whether the subject suffers from the pulmonary condition, administering to the subject a pharmaceutical compound for treatment of the pulmonary condition.

Embodiment 28. The method of embodiment 27, wherein the phosphorylation level of the peptide in the test sample is greater than the phosphorylation level of the corresponding peptide in the control sample.

Embodiment 29. The method of embodiment 27, wherein the phosphorylation level of the peptide in the test sample is lesser than the phosphorylation level of the corresponding peptide in the control sample.

Embodiment 30. The method of any one of embodiments 27-29, wherein the pharmaceutical compound is a kinase inhibitor.

Embodiment 31. The method of any one of embodiments 27-30, wherein the pharmaceutical compound is of the formula:

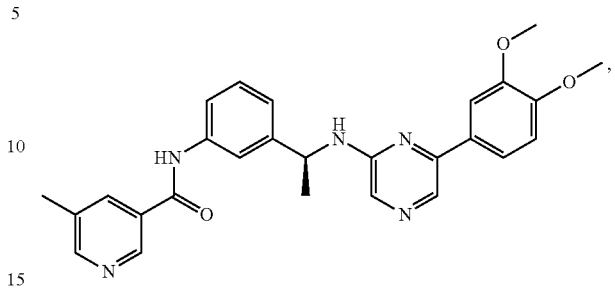

or a pharmaceutically-acceptable salt thereof.

Embodiment 32. The method of any one of embodiments 27-31, wherein the pulmonary condition is pulmonary arterial hypertension.

Embodiment 33. The method of any one of embodiments 27-32, wherein the control sample is obtained from a subject with pulmonary arterial hypertension.

Embodiment 34. The method of any one of embodiments 27-32, wherein the control sample is obtained from a subject free of pulmonary arterial hypertension.

Embodiment 35. The method of any one of embodiments 27-34, wherein the quantification of the level of the peptide in the test sample is saved to a computer system, wherein the computer system stores the phosphorylation level of the corresponding peptide in the control sample, wherein a processor of the computer system performs the comparing.

Embodiment 36. The method of any one of embodiments 27-35, wherein the peptide in the test sample and the corresponding peptide in the control sample have identical amino acid sequences.

What is claimed is:

1. A method comprising:
   a) obtaining a test sample of tissue from a subject comprising
      i) obtaining a tissue sample from a human subject, wherein the tissue sample contains a buffy coat; and
      ii) isolating a protein from the tissue sample to provide a sample of the protein;
   b) assaying the test sample to quantify in the test sample a phosphorylation level of a peptide comprising
      i) adding to the sample of the protein extracted from the buffy coat an amount of a quantification standard to provide the test sample; and
      ii) assaying the test sample to quantify in the test sample a wild type phosphopeptide of the protein extracted from the buffy coat, wherein the quantifying is based on the amount of the quantification standard, and wherein the quantification standard is a form of the phosphopeptide that is isotopically enriched to a non-natural abundance of an isotope;
   c) comparing the phosphorylation level of the peptide to a phosphorylation level of the corresponding peptide in the test sample to a control sample;
   d) based on the comparing the phosphorylation level of the peptide to the phosphorylation level of the corresponding peptide in the test sample to the control sample, determining whether the subject suffers from a pulmonary condition; and
   e) based on the determining whether the subject suffers from the pulmonary condition, administering to the subject a pharmaceutical compound for treatment of the pulmonary condition;

wherein the pulmonary condition is pulmonary arterial hypertension;
and wherein the quantification standard is an isotopically-enriched peptide selected from the following:

| SEQ ID No. | Protein | Sequence |
|---|---|---|
| 1 | IKZF3 | GLSPNNSGHDSTDTDSNHEER |
| 2 | HMHA1 | HASAAGFPLSGAASWTLGR |
| 3 | BCAS3 | HGSYDSLASDHSGQEDEEWLSQVEIVTHTGPHR |
| 4 | RHG25 | RTQTLPNRK |
| 5 | NUMA1 | RQSMAFSILNTPK |
| 6 | LEUK | RPTLTTFFGR |
| 8 | NU214 | TPSIQPSLLPHAAPFAK |
| 9 | WDR24 | IIYCSPGLVPTANLNHSVGK |
| 10 | NUMA1 | RASMQPIQIAEGTGITTR |
| 14 | MK14 | HTDDEMTGYVATR |
| 15 | ZN404 | HSHLTEHQK. |

2. The method of claim 1, wherein the phosphorylation level of the peptide in the test sample is greater than the phosphorylation level of the corresponding peptide in the control sample.

3. The method of claim 1, wherein the phosphorylation level of the peptide in the test sample is lesser than the phosphorylation level of the corresponding peptide in the control sample.

4. The method of claim 1, wherein the pharmaceutical compound is a kinase inhibitor.

5. The method of claim 1, wherein the pharmaceutical compound is of the formula:

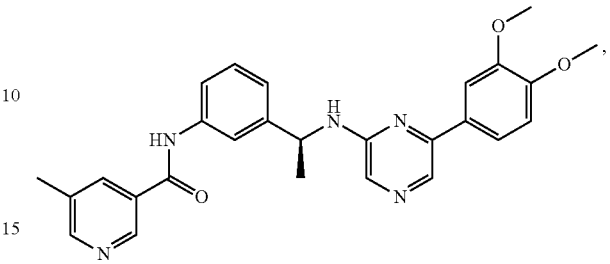

or a pharmaceutically-acceptable salt thereof.

6. The method of claim 1, wherein the control sample is obtained from a subject with pulmonary arterial hypertension.

7. The method of claim 1, wherein the control sample is obtained from a subject free of pulmonary arterial hypertension.

8. The method of claim 1, wherein the quantification of the level of the peptide in the test sample is saved to a computer system, wherein the computer system stores the phosphorylation level of the corresponding peptide in the control sample, and wherein a processor of the computer system performs the comparing.

9. The method of claim 1, wherein the peptide in the test sample and the corresponding peptide in the control sample have identical amino acid sequences.

* * * * *

UNITED STATES PATENT AND TRADEMARK OFFICE
CERTIFICATE OF CORRECTION

| | | |
|---|---|---|
| PATENT NO. | : 11,927,594 B2 | Page 1 of 1 |
| APPLICATION NO. | : 16/785434 | |
| DATED | : March 12, 2024 | |
| INVENTOR(S) | : Lawrence S. Zisman | |

It is certified that error appears in the above-identified patent and that said Letters Patent is hereby corrected as shown below:

In the Specification

<u>Column 1, Lines 16-19:</u>
"This invention was made with government support under R03HL110821 awarded by the National Heart, Lung, and Blood Institute (NHLBI). The government has certain rights in the invention."

And insert:
-- This invention was made with government support under grant number HL110821 awarded by the National Institutes of Health. The government has certain rights in the invention. --.

Signed and Sealed this
Third Day of December, 2024

Katherine Kelly Vidal
*Director of the United States Patent and Trademark Office*

SEQUENCE LISTING

```
<160> NUMBER OF SEQ ID NOS: 103

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Leu Ser Pro Asn Asn Ser Gly His Asp Ser Thr Asp Thr Asp Ser
1               5                   10                  15

Asn His Glu Glu Arg
            20

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

His Ala Ser Ala Ala Gly Phe Pro Leu Ser Gly Ala Ala Ser Trp Thr
1               5                   10                  15

Leu Gly Arg
```

<210> SEQ ID NO 3
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
His Gly Ser Tyr Asp Ser Leu Ala Ser Asp His Ser Gly Gln Glu Asp
1               5                   10                  15

Glu Glu Trp Leu Ser Gln Val Glu Ile Val Thr His Thr Gly Pro His
            20                  25                  30

Arg
```

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

```
Arg Thr Gln Thr Leu Pro Asn Arg Lys
1               5
```

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Arg Gln Ser Met Ala Phe Ser Ile Leu Asn Thr Pro Lys
1               5                   10
```

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Arg Pro Thr Leu Thr Thr Phe Phe Gly Arg
1               5                   10
```

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Asp Thr Tyr His Pro Met Ser Glu Tyr Pro Thr Tyr His Thr His Gly
1               5                   10                  15

Arg
```

```
<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Pro Ser Ile Gln Pro Ser Leu Leu Pro His Ala Ala Pro Phe Ala
1               5                   10                  15

Lys

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Ile Tyr Cys Ser Pro Gly Leu Val Pro Thr Ala Asn Leu Asn His
1               5                   10                  15

Ser Val Gly Lys
            20

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ala Ser Met Gln Pro Ile Gln Ile Ala Glu Gly Thr Gly Ile Thr
1               5                   10                  15

Thr Arg

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Phe Ser Arg Tyr Gly Arg Val Asn Tyr Val Leu Ala Arg Arg
1               5                   10                  15

<210> SEQ ID NO 12
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Ser Tyr Ser Gln Ala Ala Ser Ser Asp Ser Ala Gln Gly Ser
1               5                   10                  15

Asp Val Ser Leu Thr Ala Cys Lys
            20
```

```
<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ser Ser Ile Thr Glu Pro Glu Gly Pro Gly Gly Pro Asn Ile Gln
1               5                   10                  15

Lys

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

His Thr Asp Asp Glu Met Thr Gly Tyr Val Ala Thr Arg
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

His Ser His Leu Thr Glu His Gln Lys
1               5

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Pro Ser Gln Asn Ala Ile Ser Phe Phe Asn Val Gly His Ser Lys
1               5                   10                  15

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Cys Val Glu Glu Pro Glu Pro Glu Pro Glu Ala Ala Glu Gly Asp
1               5                   10                  15

Gly Asp Lys

<210> SEQ ID NO 18
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 18

Phe Gly Val Ser Lys Glu Lys
1               5

<210> SEQ ID NO 19
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Leu Cys Leu Val Phe Ala Leu Ile Val Phe Ser Cys Ile Tyr Gly
1               5                   10                  15

Glu Gly Tyr Ser Asn Thr His Lys Ser Lys
            20                  25

<210> SEQ ID NO 20
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Val Leu Asp Glu Glu Gly Ser Glu Arg Glu Phe Asp Glu Asp Ser Asp
1               5                   10                  15

Glu Lys Glu Glu Glu Glu Asp Thr Tyr Glu Lys
            20                  25

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Thr Gly Val Thr Ser Thr Ser Asp Ser Glu Glu Glu Gly Asp Asp Gln
1               5                   10                  15

Glu Gly Glu Lys
            20

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ile Met Val Ser Arg Ser Glu Val Asp Met Leu Lys Ile Arg
1               5                   10

<210> SEQ ID NO 23
<211> LENGTH: 21
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 23

Met His Glu Gly Asp Glu Gly Pro Gly His His His Lys Pro Gly Leu
1               5                   10                  15

Gly Glu Gly Thr Pro
            20

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Glu Glu Ser Glu Glu Ser Asp Asp Asp Met Gly Phe Gly Leu Phe
1               5                   10                  15

Asp

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Arg Glu Ser Gln Thr Ala Leu Val Ala Asn Gln Arg
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Arg Ser Pro Pro Pro Val Ser Lys
1               5

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Met Ser Leu Lys Asn Glu Pro Arg Val Asn Thr Ser Ala Leu Gln Lys
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 28

Leu Met Ser Ser Glu Gln Tyr Pro Pro Gln Glu Leu Phe Pro Arg
1               5                   10                  15

<210> SEQ ID NO 29
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Ala Ser Asp Gly Gln Tyr Glu Asn Gln Ser Pro Glu Ala Thr Ser
1               5                   10                  15

Pro Arg Ser Pro Gly Val Arg
            20

<210> SEQ ID NO 30
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Glu Ser Val Ala Ser Gly Asp Asp Arg Ala Glu Glu Asp Met Asp
1               5                   10                  15

Glu Ala Ile Glu Lys
            20

<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Arg Thr Ser Val Gln Thr Glu Asp Asp Gln Leu Ile Ala Gly Gln
1               5                   10                  15

Ser Ala Arg

<210> SEQ ID NO 32
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Leu Ser Pro Asn Asn Ser Gly His Asp Ser Thr Asp Thr Asp Ser
1               5                   10                  15

Asn His Glu Glu Arg
            20

<210> SEQ ID NO 33
<211> LENGTH: 21
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 33

Gly Leu Ser Pro Asn Asn Ser Gly His Asp Ser Thr Asp Thr Asp Ser
1               5                   10                  15

Asn His Glu Glu Arg
            20

<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

His Ala Ser Ala Ala Gly Phe Pro Leu Ser Gly Ala Ala Ser Trp Thr
1               5                   10                  15

Leu Gly Arg

<210> SEQ ID NO 35
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

His Ala Ser Ala Ala Gly Phe Pro Leu Ser Gly Ala Ala Ser Trp Thr
1               5                   10                  15

Leu Gly Arg

<210> SEQ ID NO 36
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

His Gly Ser Tyr Asp Ser Leu Ala Ser Asp His Ser Gly Gln Glu Asp
1               5                   10                  15

Glu Glu Trp Leu Ser Gln Val Glu Ile Val Thr His Thr Gly Pro His
            20                  25                  30

Arg

<210> SEQ ID NO 37
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

His Gly Ser Tyr Asp Ser Leu Ala Ser Asp His Ser Gly Gln Glu Asp
1               5                   10                  15

Glu Glu Trp Leu Ser Gln Val Glu Ile Val Thr His Thr Gly Pro His
            20                  25                  30

Arg

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Thr Gln Thr Leu Pro Asn Arg Lys
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Thr Gln Thr Leu Pro Asn Arg Lys
1               5

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Gln Ser Met Ala Phe Ser Ile Leu Asn Thr Pro Lys
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Gln Ser Met Ala Phe Ser Ile Leu Asn Thr Pro Lys
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Pro Thr Leu Thr Thr Phe Phe Gly Arg
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Pro Thr Leu Thr Thr Phe Phe Gly Arg
1               5                   10

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Thr Tyr His Pro Met Ser Glu Tyr Pro Thr Tyr His Thr His Gly
1               5                   10                  15

Arg

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Thr Tyr His Pro Met Ser Glu Tyr Pro Thr Tyr His Thr His Gly
1               5                   10                  15

Arg

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Pro Ser Ile Gln Pro Ser Leu Leu Pro His Ala Ala Pro Phe Ala
1               5                   10                  15

Lys

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Thr Pro Ser Ile Gln Pro Ser Leu Leu Pro His Ala Ala Pro Phe Ala
1               5                   10                  15

Lys

<210> SEQ ID NO 48
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ile Ile Tyr Cys Ser Pro Gly Leu Val Pro Thr Ala Asn Leu Asn His
1               5                   10                  15

Ser Val Gly Lys
            20

<210> SEQ ID NO 49
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ile Ile Tyr Cys Ser Pro Gly Leu Val Pro Thr Ala Asn Leu Asn His
1               5                   10                  15

Ser Val Gly Lys
            20

<210> SEQ ID NO 50
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Ala Ser Met Gln Pro Ile Gln Ile Ala Glu Gly Thr Gly Ile Thr
1               5                   10                  15

Thr Arg

<210> SEQ ID NO 51
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Ala Ser Met Gln Pro Ile Gln Ile Ala Glu Gly Thr Gly Ile Thr
1               5                   10                  15

Thr Arg

<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Phe Ser Arg Tyr Gly Arg Val Asn Tyr Val Leu Ala Arg
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asp Phe Ser Arg Tyr Gly Arg Val Asn Tyr Val Leu Ala Arg
1               5                   10

<210> SEQ ID NO 54
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Gly Ser Tyr Ser Gln Ala Ala Ser Ser Asp Ser Ala Gln Gly Ser
1               5                   10                  15

Asp Val Ser Leu Thr Ala Cys Lys
            20

<210> SEQ ID NO 55
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Gly Ser Tyr Ser Gln Ala Ala Ser Ser Asp Ser Ala Gln Gly Ser
1               5                   10                  15

Asp Val Ser Leu Thr Ala Cys Lys
            20

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Ser Ser Ile Thr Glu Pro Glu Gly Pro Gly Gly Pro Asn Ile Gln
1               5                   10                  15

Lys

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Ser Ser Ile Thr Glu Pro Glu Gly Pro Gly Gly Pro Asn Ile Gln
1               5                   10                  15

Lys

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

His Thr Asp Asp Glu Met Thr Gly Tyr Val Ala Thr Arg
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

His Thr Asp Asp Glu Met Thr Gly Tyr Val Ala Thr Arg
1               5                   10

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

His Ser His Leu Thr Glu His Gln Lys
1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

His Ser His Leu Thr Glu His Gln Lys
1               5

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Arg Pro Ser Gln Asn Ala Ile Ser Phe Phe Asn Val Gly His Ser Lys
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Pro Ser Gln Asn Ala Ile Ser Phe Phe Asn Val Gly His Ser Lys
1               5                   10                  15

<210> SEQ ID NO 64

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ser Cys Val Glu Glu Pro Glu Pro Glu Pro Glu Ala Ala Glu Gly Asp
1               5                   10                  15

Gly Asp Lys

<210> SEQ ID NO 65
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Cys Val Glu Glu Pro Glu Pro Glu Pro Glu Ala Ala Glu Gly Asp
1               5                   10                  15

Gly Asp Lys

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Phe Gly Val Ser Lys Glu Lys
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Phe Gly Val Ser Lys Glu Lys
1               5

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Pro Ala Arg Phe Gly Val Ser Lys Glu Lys
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 69

Pro Ala Arg Phe Gly Val Ser Lys Glu Lys
1               5                   10

<210> SEQ ID NO 70
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ala Leu Cys Leu Val Phe Ala Leu Ile Val Phe Ser Cys Ile Tyr Gly
1               5                   10                  15

Glu Gly Tyr Ser Asn Thr His Lys Ser Lys
            20                  25

<210> SEQ ID NO 71
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ala Leu Cys Leu Val Phe Ala Leu Ile Val Phe Ser Cys Ile Tyr Gly
1               5                   10                  15

Glu Gly Tyr Ser Asn Thr His Lys Ser Lys
            20                  25

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ile Tyr Gly Glu Gly Tyr Ser Asn Thr His Lys Ser Lys
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ile Tyr Gly Glu Gly Tyr Ser Asn Thr His Lys Ser Lys
1               5                   10

<210> SEQ ID NO 74
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

```
Val Leu Asp Glu Glu Gly Ser Glu Arg Glu Phe Asp Glu Asp Ser Asp
1               5                   10                  15

Glu Lys Glu Glu Glu Glu Asp Thr Tyr Glu Lys
            20                  25

<210> SEQ ID NO 75
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Val Leu Asp Glu Glu Gly Ser Glu Arg Glu Phe Asp Glu Asp Ser Asp
1               5                   10                  15

Glu Lys Glu Glu Glu Glu Asp Thr Tyr Glu Lys
            20                  25

<210> SEQ ID NO 76
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Thr Gly Val Thr Ser Thr Ser Asp Ser Glu Glu Glu Gly Asp Asp Gln
1               5                   10                  15

Glu Gly Glu Lys
            20

<210> SEQ ID NO 77
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Thr Gly Val Thr Ser Thr Ser Asp Ser Glu Glu Glu Gly Asp Asp Gln
1               5                   10                  15

Glu Gly Glu Lys
            20

<210> SEQ ID NO 78
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ile Met Val Ser Arg Ser Glu Val Asp Met Leu Lys Ile Arg
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 79

Ile Met Val Ser Arg Ser Glu Val Asp Met Leu Lys Ile Arg
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Val Ser Arg Ser Glu Val Asp Met Leu Lys Ile Arg
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Val Ser Arg Ser Glu Val Asp Met Leu Lys Ile Arg
1               5                   10

<210> SEQ ID NO 82
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Met His Glu Gly Asp Glu Gly Pro Gly His His His Lys Pro Gly Leu
1               5                   10                  15

Gly Glu Gly Thr Pro
            20

<210> SEQ ID NO 83
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Met His Glu Gly Asp Glu Gly Pro Gly His His His Lys Pro Gly Leu
1               5                   10                  15

Gly Glu Gly Thr Pro
            20

<210> SEQ ID NO 84
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

His Glu Gly Asp Glu Gly Pro Gly His His His Lys Pro Gly Leu Gly
1               5                   10                  15

Glu Gly Thr Pro
            20

<210> SEQ ID NO 85
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

His Glu Gly Asp Glu Gly Pro Gly His His His Lys Pro Gly Leu Gly
1               5                   10                  15

Glu Gly Thr Pro
            20

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Lys Glu Glu Ser Glu Glu Ser Asp Asp Asp Met Gly Phe Gly Leu Phe
1               5                   10                  15

Asp

<210> SEQ ID NO 87
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Lys Glu Glu Ser Glu Glu Ser Asp Asp Asp Met Gly Phe Gly Leu Phe
1               5                   10                  15

Asp

<210> SEQ ID NO 88
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Arg Arg Glu Ser Gln Thr Ala Leu Val Ala Asn Gln Arg
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 89

Arg Arg Glu Ser Gln Thr Ala Leu Val Ala Asn Gln Arg
1               5                   10

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ser Arg Ser Pro Pro Pro Val Ser Lys
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ser Arg Ser Pro Pro Pro Val Ser Lys
1               5

<210> SEQ ID NO 92
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Met Ser Leu Lys Asn Glu Pro Arg Val Asn Thr Ser Ala Leu Gln Lys
1               5                   10                  15

<210> SEQ ID NO 93
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Met Ser Leu Lys Asn Glu Pro Arg Val Asn Thr Ser Ala Leu Gln Lys
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ser Leu Lys Asn Glu Pro Arg Val Asn Thr Ser Ala Leu Gln Lys
1               5                   10                  15

<210> SEQ ID NO 95
<211> LENGTH: 15
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 95

Ser Leu Lys Asn Glu Pro Arg Val Asn Thr Ser Ala Leu Gln Lys
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Leu Met Ser Ser Glu Gln Tyr Pro Pro Gln Glu Leu Phe Pro Arg
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Leu Met Ser Ser Glu Gln Tyr Pro Pro Gln Glu Leu Phe Pro Arg
1               5                   10                  15

<210> SEQ ID NO 98
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Ala Ser Asp Gly Gln Tyr Glu Asn Gln Ser Pro Glu Ala Thr Ser
1               5                   10                  15

Pro Arg Ser Pro Gly Val Arg
            20

<210> SEQ ID NO 99
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ala Ala Ser Asp Gly Gln Tyr Glu Asn Gln Ser Pro Glu Ala Thr Ser
1               5                   10                  15

Pro Arg Ser Pro Gly Val Arg
            20

<210> SEQ ID NO 100
<211> LENGTH: 21
<212> TYPE: PRT
<213> ORGANISM: Artificial Sequence
<220> FEATURE:
<223> OTHER INFORMATION: Description of Artificial Sequence: Synthetic
```

```
                        peptide

<400> SEQUENCE: 100

Arg Glu Ser Val Ala Ser Gly Asp Asp Arg Ala Glu Glu Asp Met Asp
1               5                   10                  15

Glu Ala Ile Glu Lys
            20

<210> SEQ ID NO 101
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Arg Glu Ser Val Ala Ser Gly Asp Asp Arg Ala Glu Glu Asp Met Asp
1               5                   10                  15

Glu Ala Ile Glu Lys
            20

<210> SEQ ID NO 102
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ser Arg Thr Ser Val Gln Thr Glu Asp Asp Gln Leu Ile Ala Gly Gln
1               5                   10                  15

Ser Ala Arg

<210> SEQ ID NO 103
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ser Arg Thr Ser Val Gln Thr Glu Asp Asp Gln Leu Ile Ala Gly Gln
1               5                   10                  15

Ser Ala Arg
```